US007534420B2

(12) United States Patent
Bonda et al.

(10) Patent No.: US 7,534,420 B2
(45) Date of Patent: *May 19, 2009

(54) COMPOUNDS DERIVED FROM POLYANHYDRIDE RESINS WITH FILM-FORMING, UV-ABSORBING, AND PHOTOSTABLIZING PROPERTIES, COMPOSITIONS CONTAINING SAME, AND METHODS OF USING THE SAME

(75) Inventors: Craig A. Bonda, Winfield, IL (US); Anna B. Pavlovic, Elmwood Park, IL (US)

(73) Assignee: Hallstar Innovations Corp., Chicago, IL (US)

( * ) Notice: Subject to any disclaimer, the term of this patent is extended or adjusted under 35 U.S.C. 154(b) by 958 days.

This patent is subject to a terminal disclaimer.

(21) Appl. No.: 10/786,793

(22) Filed: Feb. 25, 2004

(65) Prior Publication Data

US 2005/0191249 A1    Sep. 1, 2005

(51) Int. Cl.
*A61K 8/18* (2006.01)
*C07C 255/03* (2006.01)
*C08F 267/06* (2006.01)

(52) U.S. Cl. .................. 424/59; 558/406; 525/304
(58) Field of Classification Search ............... 424/59; 558/406; 525/304
See application file for complete search history.

(56) References Cited

U.S. PATENT DOCUMENTS

| | | | |
|---|---|---|---|
| 3,215,724 A | 11/1965 | Strobel et al. | 260/465 |
| 3,215,725 A | 11/1965 | Strobel et al. | 260/465 |
| 3,272,855 A | 9/1966 | Strobel et al. | 260/465 |
| 3,275,520 A | 9/1966 | Strobel et al. | 167/90 |
| 3,337,357 A | 8/1967 | Strobel et al. | 106/178 |
| 3,445,545 A | 5/1969 | Skoultchi | 260/881 |
| 3,992,356 A | 11/1976 | Jacquet et al. | 260/47 |
| 4,107,290 A | 8/1978 | Jacquet et al. | 424/47 |
| 4,128,536 A | 12/1978 | Brodsky et al. | 427/54 |
| 4,178,303 A | 12/1979 | Lorenz et al. | 260/465 |
| 4,202,834 A | 5/1980 | Gruber et al. | 260/465 |
| 4,202,836 A | 5/1980 | Gruber et al. | 260/465.4 |
| 4,203,919 A | 5/1980 | Gruber et al. | 260/465 |
| 4,207,253 A | 6/1980 | Lorenz et al. | 260/465 |
| 4,218,392 A | 8/1980 | Lorenz et al. | 260/465 |
| 4,247,475 A | 1/1981 | Ching | 260/465 |
| 4,260,719 A | 4/1981 | Ching | 528/196 |
| 4,263,366 A | 4/1981 | Lorenz et al. | 428/332 |
| 4,264,680 A | 4/1981 | Anthony | 428/412 |
| 4,276,136 A | 6/1981 | Gruber et al. | 204/159 |
| 4,387,089 A | 6/1983 | De Polo | 424/59 |
| 4,489,057 A | 12/1984 | Welters et al. | 424/47 |
| 4,562,067 A | 12/1985 | Hopp et al. | 424/59 |
| 4,868,246 A | 9/1989 | MacLeay et al. | 525/142 |
| 5,013,777 A | 5/1991 | MacLeay et al. | 524/159 |
| 5,096,977 A | 3/1992 | MacLeay et al. | 525/343 |
| 5,210,275 A | 5/1993 | Sabatelli | 560/43 |
| 5,321,112 A | 6/1994 | Olson | 528/75 |
| 5,576,354 A | 11/1996 | Deflandre et al. | 514/685 |
| 5,681,871 A | 10/1997 | Molock et al. | 523/106 |
| 5,821,380 A | 10/1998 | Holderbaum et al. | 558/443 |
| 5,869,099 A | 2/1999 | Keller et al. | 424/486 |
| 5,882,633 A | 3/1999 | Pisson et al. | 424/59 |
| 5,972,324 A | 10/1999 | Zofchak et al. | 424/78.03 |
| 5,993,789 A | 11/1999 | Bonda et al. | 424/59 |
| 6,001,337 A | 12/1999 | Keller et al. | 424/59 |
| 6,033,649 A | 3/2000 | Gonzenbach et al. | 424/60 |
| 6,126,925 A | 10/2000 | Bonda et al. | 424/59 |
| 6,143,850 A | 11/2000 | Keller et al. | 526/304 |
| 6,284,916 B1 | 9/2001 | Bonda et al. | 560/80 |
| 6,297,300 B1 | 10/2001 | Van Nuffel | 524/91 |
| 6,306,507 B1 | 10/2001 | Brunelle et al. | 428/423.7 |
| 6,441,071 B1 | 8/2002 | Van Nuffel | 524/316 |
| 6,485,713 B1 | 11/2002 | Bonda et al. | 424/59 |
| 6,491,901 B2 | 12/2002 | Gers-Barlag et al. | 424/59 |
| 6,544,305 B2 | 4/2003 | Wood et al. | 44/275 |
| 6,610,409 B2 | 8/2003 | Pickett et al. | 428/423.7 |
| 6,689,474 B2 | 2/2004 | Pickett et al. | 428/423.7 |

(Continued)

FOREIGN PATENT DOCUMENTS

CA    1 164 886    4/1984

(Continued)

OTHER PUBLICATIONS

"Photostability of HallStar Photostable SPF 32 Sunscreen Compared to Neutrogena UVA/UVB Sunblock SPF 30," Suncare Research Laboratories, Memphis, Tennessee (Oct. 5, 2000).
Beckwith, in "The chemistry of amides: Synthesis of amides," Zabicky, J., Ed. Interscience: New York, pp. 73-185 (1970).
Bentley et al., "Medium Effects on the Rates and Mechanisms of Solvolytic Reactions," *Adv. Phys. Org. Chem.*, vol. 14, pp. 1-67 (1977).
Bentley et al., "$Y_x$ Scales of Solvent Ionizing Power," *Progr. Phys. Org. Chem.*, vol. 17, pp. 121-158 (1990).
Dimroth et al., Über Pyridinium-*N*-Phenol-Betaine und Ihre Ver Wendung zur Charakterisierung der Polarität Von LöSungsmitteln *Justus Liebigs Ann. Chem.*, vol. 661 pp. 1-37 (1963).

(Continued)

*Primary Examiner*—James O. Wilson
*Assistant Examiner*—Ebenezer Sackey
(74) *Attorney, Agent, or Firm*—Marshall, Gerstein & Borun LLP

(57) ABSTRACT

Polymers containing one or more crylene and fluorene moieties attached to the polymer backbone, sunscreen compositions including a mixture of a photoactive compound and a polymer containing one or more crylene and fluorene moieties attached to the polymer backbone are described herein. Also disclosed are methods for stabilizing a sunscreen composition and methods of filtering out ultra-violet light from a substrate by the addition of one or more of the foregoing polymers, and methods of waterproofing and forming a film with one or more of the foregoing polymer are described herein.

9 Claims, 10 Drawing Sheets

U.S. PATENT DOCUMENTS

| | | | |
|---|---|---|---|
| 6,899,866 B2 * | 5/2005 | Bonda | 424/59 |
| 2001/0022966 A1 | 9/2001 | Gers-barlag et al. | 424/59 |
| 2002/0194777 A1 | 12/2002 | Wood et al. | 44/275 |
| 2003/0000130 A1 | 1/2003 | Wood et al. | 44/275 |
| 2003/0069338 A1 | 4/2003 | Goossens et al. | 524/186 |
| 2003/0072945 A1 | 4/2003 | Pickett et al. | 428/412 |
| 2003/0130390 A1 | 7/2003 | Gorny et al. | 524/307 |
| 2003/0180542 A1 | 9/2003 | Pickett et al. | 428/423.7 |
| 2005/0186153 A1 * | 8/2005 | Bonda et al. | 424/59 |

FOREIGN PATENT DOCUMENTS

| | | |
|---|---|---|
| CA | 2204430 | 5/1996 |
| DE | 31 06 071 | 2/1982 |
| DE | 44 40 055 | 5/1996 |
| DE | 195 19 895 | 12/1996 |
| DE | 10008895 | 8/2001 |
| DE | 100 15 863 | 10/2001 |
| DE | 100 26 628 | 12/2001 |
| DE | 100 58 290 | 5/2002 |
| EP | 0 675 875 | 11/1998 |
| EP | 0 900 782 | 3/1999 |
| EP | 1129696 | 9/2001 |
| EP | 1 308 084 | 5/2003 |
| JP | 56-140959 | 4/1981 |
| WO | WO 94/14760 | 7/1994 |
| WO | WO 96/15102 | 5/1996 |
| WO | WO 00/44340 | 8/2000 |
| WO | WO 01/16224 | 3/2001 |
| WO | WO 01/57125 | 8/2001 |
| WO | WO 01/90233 | 11/2001 |
| WO | WO 01/92395 | 12/2001 |
| WO | WO 02/42368 | 5/2002 |
| WO | WO 2004/031294 | 4/2004 |

OTHER PUBLICATIONS

Fainberg et al., "Correlation of Solvolysis Rates. III. t-Butyl Chloride in a Wide Range of Solvent Mixtures," *J. Am Chem. Soc.*, vol. 78 pp. 2770-2777 (1956).

Grunwald et al., "The Correlation of Solvolysis Rates," J. Am. Chem. Soc., vol. 70, pp. 846-854 (1948).

Haslem, "Recent Developments in Methods For the Esterification and Protection of the Carboxyl Group," *Tetrahedron*, vol. 36, pp. 2409-2433 (1980).

Kamlet et al., "An Examination of Linear Solvation Energy Relationships," *Progr. Phys. Org. Chem.*, vol. 13, pp. 485-630 (1981).

Kosower, "The Effect of Solvent on Spectra. I. A New Empirical Measure of Solvent Polarity Z-Values," *J. Am Chem. Soc.*, vol. 80, pp. 3253-3260 (1958).

McNaught et al., "IUPAC Compendium of Chemical Terminology," $2^{nd}$ Ed. (1997).

Reichardt, "Solvents and Solvent Effects in Organic Chemistry," 2nd Ed., Chap. 7: Empirical Parameters of Solvent Polarity, VCH Publishers, New York, New York (1998).

Sayre et al., "Photostability Testing of Avobenzone," Allured's Cosmetics & Toiletries Magazine, vol. 114, No. 5, pp. 85-91 (May 1999).

Tarras-Wahlberg et al., "Changes in Ultraviolet Absorption of Sunscreens After Ultraviolet Radiation," *J. Investigative Dermatology*, vol. 113, No. 4, pp. 547-553 (1999).

Turro, *Modern Molecular Photochemistry* Benjamin/Cummings Publ. Co., Menlo Park, California, pp. 296-361 (1991).

International Search Report for International Application No. PCT/US2005/004591 dated Jun. 22, 2005 by the European Patent Office (3 pages).

* cited by examiner

COMPOUNDS DERIVED FROM POLYANHYDRIDE RESINS WITH FILM-FORMING, UV-ABSORBING, AND PHOTOSTABLIZING PROPERTIES, COMPOSITIONS CONTAINING SAME, AND METHODS OF USING THE SAME

BACKGROUND OF THE INVENTION

1. Field of the Invention

The invention relates to compounds, and methods to increase the UV-absorbance, water resistance, and photostability of a variety of compositions. More particularly, the invention relates to cyanodiphenylacrylate ("Crylene") and/or cyanofluorenylidene acetate ("Fluorene") polymer compounds and compositions containing the same, and methods of using them that include a method of protecting a material from ultra-violet radiation, a method of waterproofing, a method of forming a film, and a method of photostabilizing a photounstable compound.

2. Brief Description of Related Technology

It is well known that ultraviolet radiation (light) having a wavelength from about 280 nm or 290 nm to about 320 nm (UV-B) is harmful to human skin, causing burns that are detrimental to the development of a good sun tan. UV-A radiation (about 320 nm to about 400 nm), while producing tanning of the skin, also can cause damage, particularly to very lightly-colored or sensitive skin, leading to reduction of skin elasticity and wrinkles. Therefore, a sunscreen composition for use on human skin preferably includes both a UV-A and a UV-B filter to prevent most of the sunlight within the full range of about 280 nm or 290 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to color fading, loss of gloss; and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals.

UV-A and UV-B filters can also be used to absorb UV radiation to protect a pigmented coating. The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL MCX; octyl salicylate; and oxybenzone.

The organic UV-A filters most commonly used in commercial sunscreen compositions are the dibenzoylmethane derivatives, particularly 4-(1,1-dimethylethyl)-4'-methoxydibenzoylmethane (also called avobenzone, sold under the brand name PARSOL 1789). Other dibenzoylmethane derivatives described as UV-A filters are disclosed in U.S. Pat. Nos. 4,489,057, 4,387,089 and 4,562,067, the disclosures of which are hereby incorporated herein by reference. It is also well known that the above described UV-A filters, particularly the dibenzoylmethane derivatives, can suffer from rapid photochemical degradation, when used alone or when combined with the above-described most commercially used UV-B filters.

Typically, the above-described UV-B filters are combined with the above described UV-A filters in a solution with other lipophilic or oily ingredients. This solution of oily ingredients, known to formulators of cosmetic products including sunscreens as the "oil phase," is typically, but not necessarily, dispersed with the help of emulsifiers and stabilizers into an aqueous solution composed primarily of water, to make an emulsion which becomes a final cream or lotion form of a sunscreen composition.

The performance of a photoactive compound or a combination of photoactive compounds in a sunscreen composition has been extremely difficult to predict based on the levels of photoactive compounds in the formulation, particularly when the formulation includes one or more photoactive compounds that suffer from relatively rapid photodegradation, such as avobenzone. Because of this, each formulation has required expensive laboratory testing to determine the UV absorbance, as a function of time (quantity) of exposure of the formulation to UV radiation. Moreover, a particularly difficult problem is presented when one photoactive compound in a sunscreen composition acts to increase the rate of photodegradation of another photoactive compound in the composition. This can be accomplished in a number or ways, including a bimolecular reaction between two photoactive compounds and a lowering of the threshold energy needed to raise a photoactive compound to its excited state. For example, when avobenzone is combined with octyl methoxycinnamate a bimolecular pathway leads to the rapid photodegradation of both the dibenzoylmethane derivative and the octyl methoxycinnamate.

Methods and compositions for stabilizing photoactive compounds, such as dibenzoylmethane derivatives, with the use of octocrylene and fluorene are described in the commonly-assigned U.S. Pat. Nos. 5,993,789, 6,113,931, 6,126,925, and 6,284,916, the disclosures of which are hereby incorporated herein by reference. Other methods of stabilizing a dibenzoylmethane derivative include the addition of an α-cyano-β,β-diphenylacrylate compound to a sunscreen composition including a dibenzoylmethane derivative. See, Deflandre et al, U.S. Pat. No. 5,576,354 and Gonzenbach et al., U.S. Pat. No. 6,033,649.

SUMMARY

Figure 1:
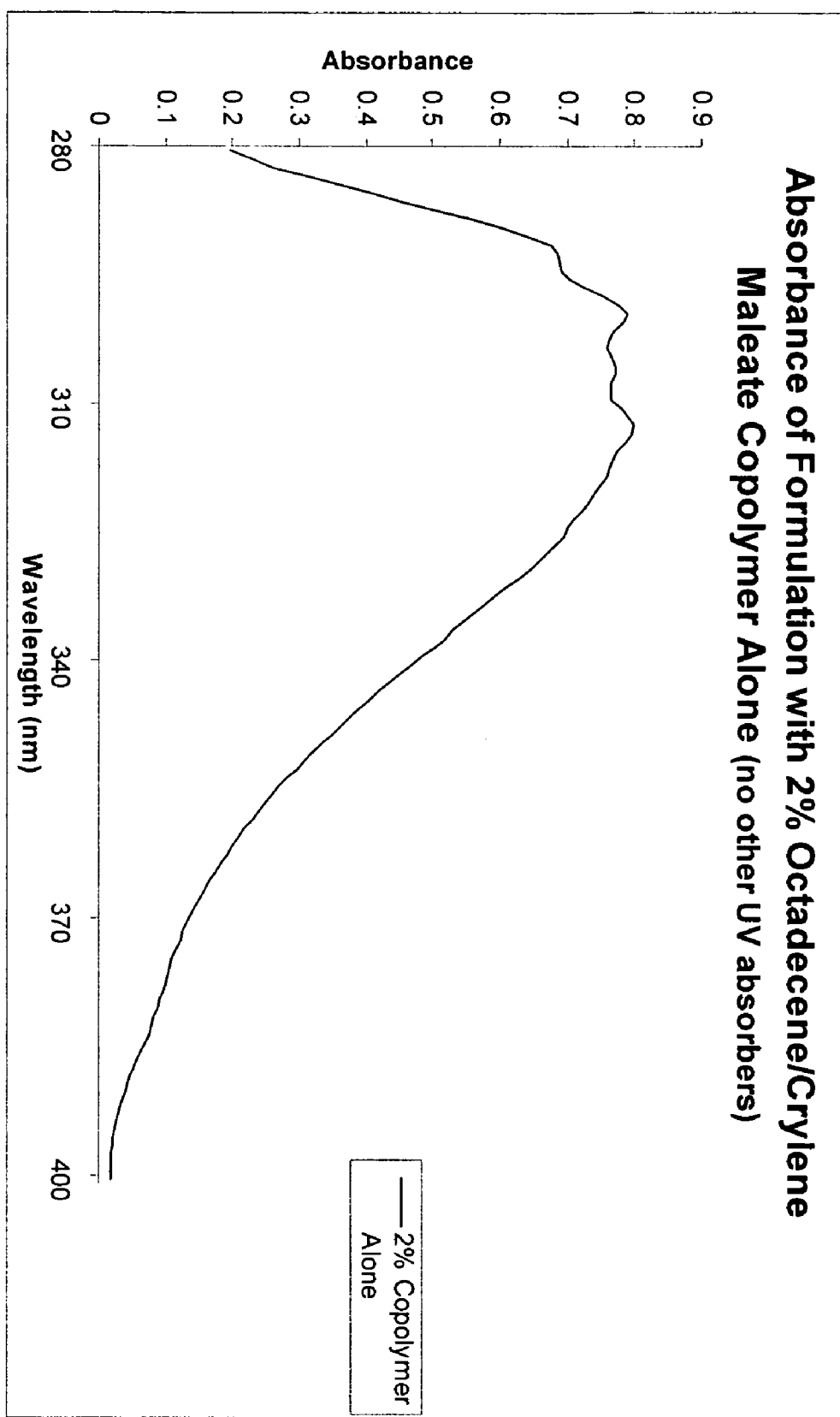
FIG. 1 is a graph of the absorbance of a sunscreen composition that includes 2% Octadecene/Crylene maleate copolymer as the only UV-absorbing compound, from a wavelength of 280 nm to 400 nm.

One aspect of the compounds, compositions, and methods disclosed herein is to provide a polymeric compound having a crylene moiety (2-cyano-3,3-diphenylacrylic acid) attached to the polymer backbone.

Another aspect of the compounds, compositions, and methods disclosed herein is to provide a sunscreen composition that includes a UV-absorbing polymeric compound having a crylene moiety (2-cyano-3,3-diphenylacrylic acid) attached to the polymer backbone.

Another aspect of the compounds, compositions, and methods disclosed herein is to provide a method of reducing or eliminating an amount of ultra-violet light that contacts a substrate by disposing between the source of ultra-violet light and the substrate, or applying to the substrate a polymeric compound having a crylene moiety (2-cyano-3,3-diphenylacrylic acid) attached to the polymer backbone.

Another aspect of the compounds, compositions, and methods disclosed herein is to provide a method of waterproofing a substrate surface by applying thereto a polymeric compound having a crylene moiety (2-cyano-3,3-diphenylacrylic acid) attached to the polymer backbone.

Another aspect of the compounds, compositions, and methods disclosed herein is to provide a method of protecting a photodegradable material against photodegradation by applying thereto a polymeric compound having a crylene moiety (2-cyano-3,3-diphenylacrylic acid) attached to the polymer backbone.

Another aspect of the compounds, compositions, and methods disclosed herein is to provide a method of forming a UV-absorbing film on a substrate surface by applying thereto film or coating containing a polymeric compound having a crylene moiety (2-cyano-3,3-diphenylacrylic acid) attached to the polymer backbone.

Another aspect of the compounds, compositions, and methods disclosed herein is to provide a method for photostabilizing a sunscreen composition including a photoactive compound by the addition of a photostabilizing effective amount of a polymeric compound having a crylene moiety (2-cyano-3,3-diphenylacrylic acid) attached to the polymer backbone.

Yet another aspect of the compounds, compositions, and methods disclosed herein is to provide a polymeric compound having a fluorene moiety (cyano(9H-fluoren-9-ylidene)acetic acid) attached to the polymer backbone.

Another aspect of the compounds, compositions, and methods disclosed herein is to provide a sunscreen composition that includes a polymeric compound having a fluorene moiety (cyano(9H-fluoren-9-ylidene)acetic acid) attached to the polymer backbone.

Another aspect of the compounds, compositions, and methods disclosed herein is to provide a method of reducing or eliminating an amount of ultra-violet light that contacts a substrate by disposing between the source of ultra-violet light and the substrate, or applying to the substrate a polymeric compound having a fluorene moiety (cyano(9H-fluoren-9-ylidene)acetic acid) attached to the polymer backbone.

Another aspect of the compounds, compositions, and methods disclosed herein is to provide a method of waterproofing a substrate surface by applying thereto a polymeric compound having a fluorene moiety (cyano(9H-fluoren-9-ylidene)acetic acid) attached to the polymer backbone.

Another aspect of the compounds, compositions, and methods disclosed herein is to provide a method of protecting a photodegradable material against photodegradation by applying thereto a polymeric compound having a fluorene moiety (cyano(9H-fluoren-9-ylidene)acetic acid) attached to the polymer backbone.

Another aspect of the compounds, compositions, and methods disclosed herein is to provide a method of forming a UV-absorbing film on a substrate surface by applying thereto film or coating containing a polymeric compound having a fluorene moiety (cyano(9H-fluoren-9-ylidene)acetic acid) attached to the polymer backbone.

Another aspect of the compounds, compositions, and methods disclosed herein is to provide a method for photostabilizing a sunscreen composition including a photoactive compound by the addition of a photostabilizing effective amount of a polymeric compound having a fluorene moiety (cyano(9H-fluoren-9-ylidene)acetic acid) attached to the polymer backbone.

Still another aspect of the compounds, compositions, and methods disclosed herein is to provide a polymeric compound having a crylene moiety (2-cyano-3,3-diphenylacrylic acid) and a fluorene moiety (cyano(9H-fluoren-9-ylidene) acetic acid) attached to the polymer backbone.

Another aspect of the compounds, compositions, and methods disclosed herein is to provide a sunscreen composition that includes a polymeric compound having a crylene moiety (2-cyano-3,3-diphenylacrylic acid) and a fluorene moiety (cyano(9H-fluoren-9-ylidene)acetic acid) attached to the polymer backbone.

Another aspect of the compounds, compositions, and methods disclosed herein is to provide a method of reducing or eliminating an amount of ultra-violet light that contacts a substrate by disposing between the source of ultra-violet light and the substrate, or applying to the substrate a polymeric compound having a crylene moiety (2-cyano-3,3-diphenylacrylic acid) and a fluorene moiety (cyano(9H-fluoren-9-ylidene)acetic acid) attached to the polymer backbone.

Another aspect of the compounds, compositions, and methods disclosed herein is to provide a method of waterproofing a substrate surface by applying thereto a polymeric compound having a crylene moiety (2-cyano-3,3-diphenylacrylic acid) and a fluorene moiety (cyano(9H-fluoren-9-ylidene)acetic acid) attached to the polymer backbone.

Another aspect of the compounds, compositions, and methods disclosed herein is to provide a method of protecting a photodegradable material against photodegradation by applying thereto a polymeric compound having a crylene moiety (2-cyano-3,3-diphenylacrylic acid) and a fluorene moiety (cyano(9H-fluoren-9-ylidene)acetic acid) attached to the polymer backbone.

Another aspect of the compounds, compositions, and methods disclosed herein is to provide a method of forming a UV-absorbing film on a substrate surface by applying thereto film or coating containing a polymeric compound having a crylene moiety (2-cyano-3,3-diphenylacrylic acid) and a fluorene moiety (cyano(9H-fluoren-9-ylidene)acetic acid) attached to the polymer backbone.

Another aspect of the compounds, compositions, and methods disclosed herein is to provide a method for photostabilizing a sunscreen composition including a photoactive compound by the addition of a photostabilizing effective amount of a polymeric compound having a crylene moiety (2-cyano-3,3-diphenylacrylic acid) and a fluorene moiety (cyano(9H-fluoren-9-ylidene)acetic acid) attached to the polymer backbone.

DETAILED DESCRIPTION OF THE PREFERRED EMBODIMENT

Sunscreen compositions typically include one or more photoactive compounds that can absorb UV radiation, and often sunscreen compositions include a variety of photoactive compounds to absorb UV-radiation over the entire UV range (UV-A and UB-B range). Compounds and compositions that include the photoactive moieties crylene (2-cyano-3,3-diphenylacrylic acid) and/or fluorene (cyano(9H-fluoren-9-ylidene)acetic acid), and methods of use of such compounds are described herein.

The general structure of a crylene moiety (2-cyano-3,3-diphenylacrylic acid) is shown below:

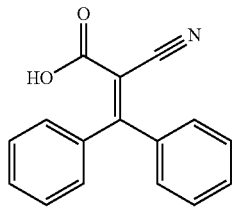

Optionally, each of the aromatic rings on the core crylene moiety can be substituted with various functional groups. It has been found that the attachment of the crylene moiety, such as is found in the UV-absorber Octocrylene (shown below as A), may be attached to a polymer to convert the polymer into a compound capable of absorbing and/or dissipating UV radiation, as well as to photostabilize another UV-absorbing compound.

An α-cyano-β,β-diphenylacrylate compound is known to quench (accept the excited state energy) of an excited photoactive compound (see, e.g., the commonly assigned U.S. patent application Ser. Nos. 10/241,388, 10/361,223, and 10/785,271 (now U.S. Pat. No. 6,899,866). Without intending to be limited to any particular mechanism by which an α-cyano-β,β-diphenylacrylate compound is able to quench the excited state of photoactive compound, it is theorized that the α-cyano-β,β-diphenylacrylate compound accepts the excited state energy and dissipates the energy kinetically in the form of rapid isomerizations. This process is shown below:

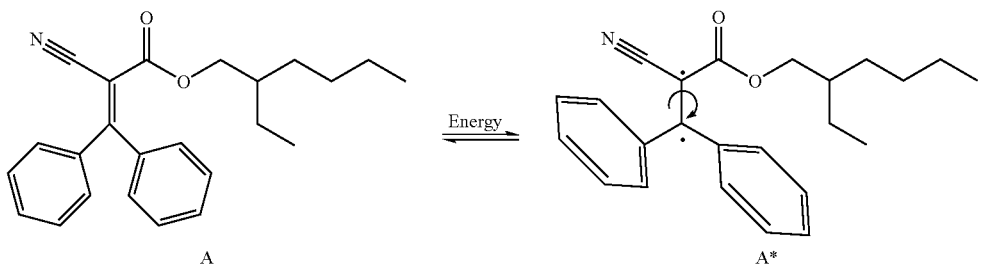

wherein the α-cyano-β,β-diphenylacrylate compound (octocrylene shown above as structure A), accepts the triplet excited state energy from a photoactive compound and forms a diradical (shown above as structure A*) at the α and β positions of the acrylate, which converts the double bond into a single bond and allows for the free rotation of the phenyl groups. This rotation occurs rapidly and efficiently to dissipate any excited state energy accepted by the α-cyano-β,β-diphenylacrylate compound from the photoactive compound. In solution (e.g., a sunscreen composition), a key limitation on the ability of a compound to photostabilize another compound is the ability of the two compounds to come into contact with one another.

The general structure of a fluorene moiety (cyano(9H-fluoren-9-ylidene)acetic acid) is shown below:

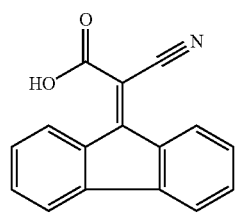

Optionally, each of the aromatic rings on the core crylene moiety can be substituted with various functional groups. It has been found that a flourene moiety, such as is found in 2-ethylhexyl cyano(9H-fluoren-9-ylidene) acetate), hereinafter referred to as octofluorene, as shown below as structure B, may be attached to a polymer to convert the polymer into a compound capable of absorbing and/or dissipating UV radiation, as well as photostabilizing another UV-absorbing compound. Without intending to be limited to any particular mechanism by which such compounds are able to quench (accept the excited state energy) an excited photoactive compound, it is theorized that a polymer having a fluorene moiety attached thereto, for example a 9-methylene-9H-fluorene, accepts the excited state energy from another UV-absorbing compound in an excited state and dissipates the energy kinetically in the form of rapid isomerizations. An example of this process is shown below:

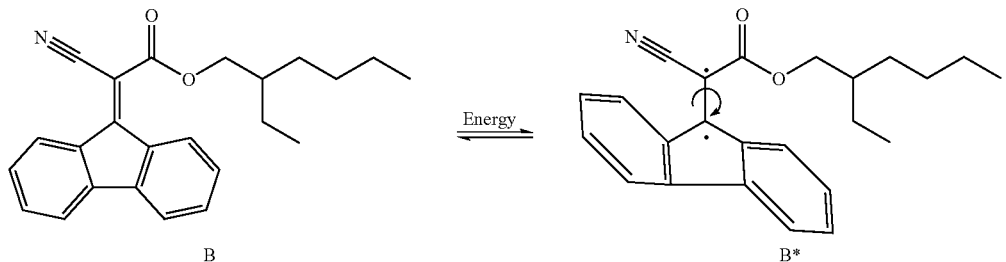

B ⇌ B* wherein octofluorene (shown above as structure B) accepts the triplet excited state energy and forms a diradical (shown above as structure B*) at the α and β positions of the acrylate, which converts the double bond into a single bond and allows for free rotation about the single bond. This rotation occurs rapidly and efficiently to dissipate excited state energy accepted by a derivative of fluorene (a compound that includes the fluorene moiety).

It has also been discovered that the novel UV-absorbing and photostabilizing compounds disclosed in the commonly assigned U.S. patent application Ser. Nos. 10/246,434, 10/458,286, 10/302,423, and 10/385,833, the disclosures of which are hereby incorporated by reference, may be attached to a polymer molecule to provide other novel UV-absorbing and photostabilizing polymers. It has also been found that the polymer resulting from the attachment to the polymer backbone of the photostabilizing compounds disclosed in the above-listed applications would create a polymer that can absorb UV-radiation and photostabilize one or more other photoactive compounds in a UV-absorbing composition.

In accordance with another important "tether" embodiment of the compounds, compositions, and methods disclosed herein, it has also been discovered that by attaching a tether to the crylene and/or fluorene moieties and attaching the crylene and/or fluorene moieties to the polymer backbone via the tether, the crylene and fluorene moieties are thereby spaced from the polymer backbone by attaching a tether (a spacer) so that there is less steric interference, to provide a more effective and efficient energy absorption and dissipation of the excited state energy via the aromatic ring(s) spinning about the tether (spacer). Suitable tether molecules include diols, diamino compounds, or any compound with two or more functional groups, wherein at least one functional group can be covalently attached to the carboxylic acid on the crylene and/or fluorene moieties (e.g., an alcohol, amine, carboxylic acid, a sulfide), and another functional group that can be covalently bonded to the polymer backbone. Nonlimiting examples of suitable tethers include alkyl diols (e.g., neopentyl glycol), alkyl diamines (e.g., 1,5-diaminopentane), and alkyl amino alcohols (5-amino-1-pentanol). Another advantage to using a tether is the potential to add additional hydrophobic or hydrophilic groups on the tether to influence the solubility properties of the resulting polymer.

Any polymers may be used in this "tether" embodiment so long as it is capable of attachment of a tether molecule to its polymer backbone. Exemplary polymers that are useful include those having on its backbone a free alcohol, carboxylic acid, amine, and/or amide wherein these functional groups can be covalently bonded to a crylene and/or fluorene moiety, or a suitable tether. Copolymers of an α-olefin and maleic anhydride are particularly suitable for the attachment of a crylene and/or fluorene moiety. Without intending to be limited to a particular mechanism of attachment, it is theorized that a crylene and/or a fluorene moiety is covalently bonded to a copolymer of an α-olefin and maleic anhydride is shown below for poly(octadecene-1-co-maleic anhydride):

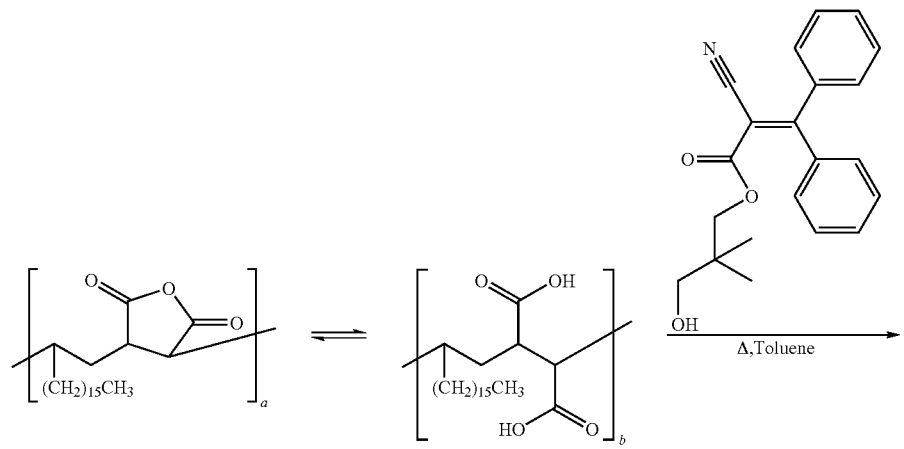

-continued

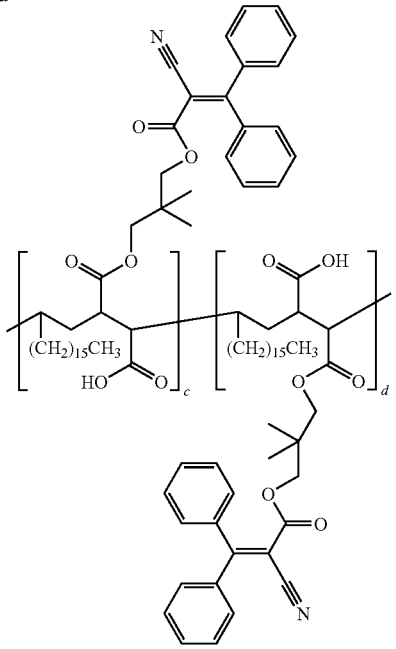

wherein a and b are each in the range of 2 to 5000; c and d are each in the range of 0 to 5000; and sum of c plus d is at least 2.

Copolymers that are suitable to be covalently bonded crylene and/or fluorene moiety (with or without a tether) include, but are not limited to, Poly(alpha olefin-co-maleic anhydride), which can be prepared according the procedures set forth in U.S. Pat. Nos. 3,860,700, 6,358,892, and U.S. Pat. Reissue No. 28,475, the disclosures of which are hereby incorporated by reference. Examples of these resins include Poly(octadecene-1-co-maleic anhydride) resin (PA-18 available from Chevron Chemicals Co., San Francisco, Calif.), Poly(styrene-co-maleic anhydride) resin (SMA® resins, available from Atofina Chemicals Inc. Philadelphia, Pa.), Poly(ethylene-co-maleic anhydride) resin (EMA®, available from Monsanto, St. Louis, Mo.), Poly(isobutene-co-maleic anhydride) resin (ISOBAM® available form Kuraray Co. Ltd., Osaka, Japan), and Poly(methylvinylether-co-maleic anhydride) resin (Gantrez® An available from ISP, Wayne, N.J.). Alternatively, a mixture of alpha olefins may be used to form the maleic anhydride copolymer, and thereby provide a versatile polymer with a number of different properties (e.g., waterproofing and/or lubricating). Alternately mixtures of alpha olefins can be used (e.g., Ketjenlube® resins available from Akzo Nobel Co., Dobbs Ferry, N.Y.). Maleic anhydride polymers made with a mixture of alpha olefins are described in U.S. Pat. Nos. 3,461,108, 3,560,455, 3,560,456, 3,560,457, 3,580,893, 3,706,704, 3,729,450, and 3,729,451, the disclosures of which are hereby incorporated by reference. Preferably, the polymer used according to the invention is a Poly(alpha olefin-co-maleic anhydride) resin; more preferably, the polymer is a Poly(octadecene-1-co-maleic anhydride) resin.

Polymer backbone molecules of a particular polymer generally exists as a mixture of polymer molecules of different chain lengths, wherein the polymer is described as having a chain length that is an average of the chain lengths of the adjacent polymer molecules. Likewise, the molecular weight of a particular polymer can be determined in a number of ways, including a determination of the Weight Average Molecular Weight ($M_W$), which is the summation of the weights of each different sized polymer in a mixture multiplied by the mole fraction of that polymer size in the polymer mixture. Nonlimiting examples of methods of calculating a given polymer's Weight Average Molecular Weight include diffusion, sedimentation, flow birefringence, and light scattering. Preferably, a polymer disclosed herein has a Weight Average Molecular Weight is the range of about 20,000 to about 130,000 grams/mole, more preferable in the range of about 30,000 to about 110,000 grams/mole.

Sunscreen compositions containing one or more photoactive compounds, such as a dibenzoylmethane derivative UV-A filter compound, and a polymer containing one or more crylene and/or fluorene moieties covalently bonded to the polymer backbone are also described herein. One aspect of the sunscreen compositions described herein are methods of photostabilizing a sunscreen composition including a dibenzoylmethane derivative, such as 4-(1,1-dimethylethyl)-4'-methoxydibenzoylmethane (PARSOL® 1789), wherein one or more photoactive compounds present in a sunscreen composition (e.g., avobenzone) are made more photostable by the addition of a polymer containing one or more crylene and/or fluorene moieties covalently bonded to the polymer backbone. Further disclosed herein are methods for filtering out ultra-violet light from human skin including the step of applying to the skin a cosmetically acceptable composition including a polymer containing one or more crylene and/or fluorene moieties covalently bonded to the polymer backbone. Also disclosed herein is a method of waterproofing a material by forming a film on a surface of a material, wherein the film includes a polymer containing one or more of crylene and/or fluorene moieties attached to the polymer.

A photoactive compound can be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for avobeozone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compound).

In commonly assigned U.S. patent application Ser. Nos. 10/241,388, 10/361,223, and 10/785,271 (now U.S. Pat. No. 6,899,866), the disclosures of which are hereby incorporated by reference, it was found that the addition of an α-cyano-β, β-diphenylacrylate compound and a diester or polyester of naphthalene dicarboxylic acid were able to stabilize a photounstable UV-absorbing compound, e.g., a dibeazoylmethane derivative, such as PARSOL 1789, in a sunscreen composition. It has surprisingly been found that sunscreen compositions containing a combination of (1) a polymer containing one or more crylene and/or fluorene moieties covalently bonded to the polymer backbone, and (2) a diester or polyester of naphthalene dicarboxylic acid can significantly increase the photostability of any photounstable component(s) present therein (e.g., a dibenzoylmethane derivative). Without intending to be limited to any particular mechanism of achieving this increase in photostability, it is believed that a diester or polyester of naphthalene dicarboxylic acid stabilizes a dibenzoylmethane derivative by accepting the triplet energy of the dibenzoylmethane derivative once the dibenzoylmethane derivative has reached an excited state as a result of the absorption of ultra-violet light. Once a dibeazoylmethane derivative is excited, it is prone to degrade according to a number of pathways; however, the degradation of the dibenzoylmethane derivative can be substantially reduced or prevented by the use of a diester or polyester of naphthalene dicarboxylic acid to quench (accept) the triplet excited state energy present in an excited dibenzoylmethane molecule. Thus, in one pathway of degradation, a dibenzoylmethane derivative is excited to its triplet state and the excited state triplet energy is released in a bond breaking step, thereby preventing the dibenzoylmethane derivative from further accepting ultra-violet radiation. A diester or polyester of naphthalene dicarboxylic acid may stabilize a dibenzoylmethane derivative by accepting the triplet state (excited state) energy of the excited dibenzoylmethane derivative in such a way as to convert the excited dibenzoylmethane derivative back to a ground state that is capable of reaccepting (or accepting additional) ultra-violet radiation (energy transfer).

For this process to work continuously, the diester or polyester of naphthalene dicarboxylic acid must transfer or convert the energy that was accepted from the excited dibenzoylmethane derivative. Without intending to be limited to a particular mechanism, it is believed that when a diester or polyester of naphthalene dicarboxylic acid is excited to its triplet state, it dissipates the triplet excited state energy through vibrations (e.g., as heat), which in this group of molecules is a relatively slow mode of dissipating energy. It has been found, quite surprisingly, that by the addition of a polymer containing one or more crylene and/or fluorene moieties covalently bonded to the polymer backbone, such a compound is able to accept triplet excited state energy from an excited diester or polyester of naphthalene dicarboxylic acid. Thus, according to one possible mechanism, the efficiency of the dissipation of the excited state energy in an excited diester or polyester of naphthalene dicarboxylic acid is greatly improved by a transfer of energy from an excited diester or polyester of naphthalene dicarboxylic acid to the polymer containing one or more crylene and/or fluorene moieties.

Thus, preferably, a composition disclosed herein includes a diester or polyester of naphthalene dicarboxylic acid selected from the group consisting of compounds of formulae (XIII) and (XIV), and combinations thereof:

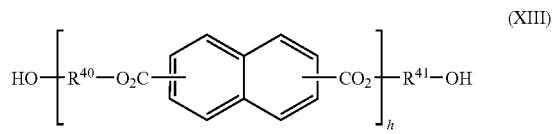

(XIII)

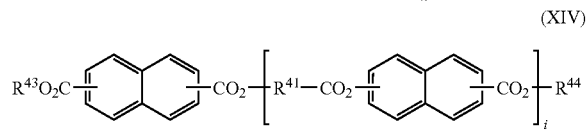

(XIV)

wherein $R^{43}$ and $R^{44}$ are the same or different and selected from the group consisting of $C_1$-$C_{22}$ alkyl groups, diols having the structure HO—$R^{41}$—OH, and polyglycols having the structure HO—$R^{40}$—(—O—$R^{41}$—)$_j$—OH; wherein each $R^{40}$ and $R^{41}$ is the same or different and selected from the group consisting of $C_1$-$C_6$ straight or branched chain alkyl groups; and wherein h and j are each in a range of 1 to 100 and i is in a range of 0 to 100.

The method of preparation of particularly useful diesters and polyesters of naphthalene dicarboxylic acid and the use of diesters and polyesters of naphthalene dicarboxylic acid in a sunscreen composition are described in U.S. Pat. Nos. 5,993,789 and 6,284,916, the disclosures of which are hereby incorporated herein by reference. Preferably, a UV-absorbing composition that includes a diester or polyester of naphthalene dicarboxylic acid includes a diester of formula (XIV) wherein $R^{43}$ and $R^{44}$ are 2-ethylhexane and p is 0. Preferably, the UV-absorbing compositions disclosed herein include a diester or polyester of naphthalene dicarboxylic acid in a range of about 0.1% to about 15% by weight of the total weight of the composition.

A sunscreen composition can be combined into a cosmetically acceptable carrier, optionally including emollients, stabilizers, emulsifiers, such as those known in the art, and combinations thereof. These additives can be used in preparing an emulsion from an aqueous composition and a mixture of a UV filter composition that includes one or more photoactive compounds and a solvent or a solvent combination that includes one or more organic solvents. When made, preferably the emulsion is an oil-in-water emulsion, wherein the oil phase is primarily formed from a mixture of the filter system and solvent system.

A typical sunscreen composition includes one or more photoactive compounds, wherein a photoactive compound acts to absorb UV radiation and thereby protect the substrate (e.g., human skin) from the harmful effects of UV radiation. The absorption process causes a photoactive compound to reach an excited state, wherein the excited state is characterized by the presence of excited energy (e.g., singlet energy or triplet energy), as compared to the ground state of the photoactive compound. Once a photoactive compound reaches an excited state there exists a number of pathways by which the excited photoactive compound can dissipate its excess energy (e.g., triplet energy), however, many of those pathways adversely affect the ability of the photoactive compound to further absorb UV radiation.

It has surprisingly been found that the addition of polymers containing one or more crylene and/or fluorene moieties covalently bonded to the polymer backbone increase the photostability of the sunscreen composition. Without intending to be limited to any particular mechanism by which a such compounds are able to quench (accept the excited state energy) an excited photoactive compound, it is believed that, for example the crylene and fluorene moieties accept the excited state energy and dissipates the energy kinetically in the form of rapid isomerizations. An example of this process is shown below wherein the PA-18 polymer (poly(octadecene-1-co-maleic anhydride)) having both crylene and fluorene moieties attached to the polymer backbone:

respond to UV radiation photoelectrically by rapid photodegradation can benefit highly from the compositions and methods disclosed herein, even though the benefits of the compositions and methods disclosed herein are not limited to such compounds. Photostability is a potential problem with all UV filters because they are deliberately selected as UV-absorbing molecules. In other applications, a photoactive compound may be a pigment or a dye (e.g., a hydrophobic dye).

UV filters include compounds selected from the following categories (with specific examples) including: p-aminoben-

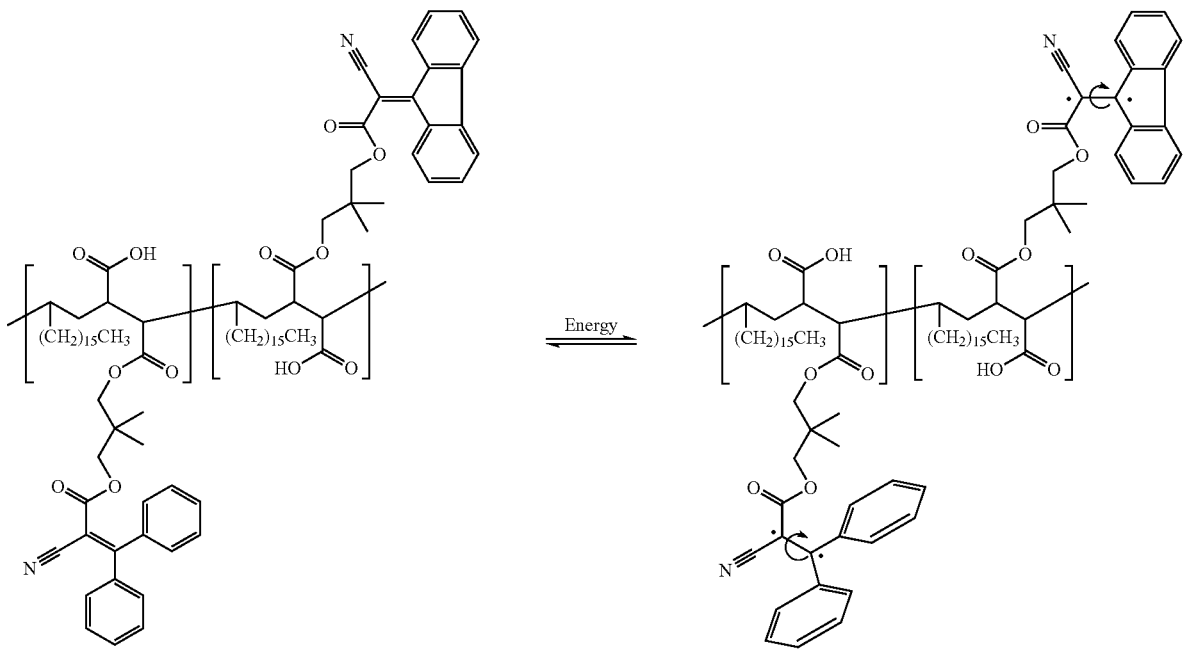

The polymer accepts the triplet excited state energy from a photoactive compound and forms a diradical at the α and β positions of the acrylate, which converts the double bond into a single bond and allows for free rotation of the phenyl groups or fluorene group about the single bond. This rotation occurs rapidly and efficiently to dissipate excited state energy accepted by a derivative of fluorene.

Commonly-assigned U.S. Pat. Nos. 6,485,713 and 6,537, 529, the disclosures of which are hereby incorporated herein by reference, describe compositions and methods for increasing the photostability of photoactive compounds in a sunscreen composition, e.g., by the addition of polar solvents to the oil phase of a composition. It has been found, quite surprisingly, that by increasing the polarity of the oil phase of a sunscreen composition including a polymer containing one or more crylene and/or fluorene moieties covalently bonded to the polymer backbone, the stability of the sunscreen composition is increased. Thus, in a sunscreen disclosed herein, preferably, one or more of a highly polar solvent is present in the oil-phase of the composition. Preferably, a sufficient amount of a polar solvent is present in a sunscreen composition to raise the dielectric constant of the oil-phase of the composition to a dielectric constant of at least about 7, preferably at least about 8.

A photoactive compound is one that responds to light photoelectrically. In the compositions disclosed herein, a photoactive compound is one that responds to UV radiation photoelectrically. For example, photoactive compounds that zoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid, and combinations thereof.

For a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3 diphenylacrylate; 10% or less), octyl methoxycinnamate- (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds and preferred concentrations (percent by weight of the total cosmetic sunscreen composition) include diethanolamine methoxycinnamate (10% or less), ethyl-[bis(hydroxypropyl)] aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine.(10% or less, also called TINOSORB S).

All of the above-described UV filters are commercially available. For example, suitable commercially-available organic UV filters are identified by trade name and supplier in Table I below:

TABLE I

| CTFA Name | Trade Name | Supplier |
|---|---|---|
| benzophenone-3 | UVINULM-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

The term "alkyl" herein refers to straight- and branched-chain hydrocarbon groups, preferably containing one to thirty carbon atoms. Examples of alkyl groups are $C_1$-$C_4$ alkyl groups. As used herein the designation $C_x$-$C_y$, wherein x and y are integers, denotes a group having from x to y carbon atoms, e.g., a $C_1$-$C_4$ alkyl group is an alkyl group having one to four carbon atoms. Nonlimiting examples of alkyl groups include, methyl, ethyl, n-propyl, isopropyl, n-butyl, sec-butyl (2-methylpropyl), and t-butyl (1,1-dimethylethyl).

The term "cycloalkyl" as used herein refers to an aliphatic cyclic hydrocarbon group, preferably containing three to eight carbon atoms. Nonlimiting examples of cycloalkyl groups include cyclopropyl, cyclobutyl, cyclopentyl, and cyclohexyl.

The terms "substituted alkyl" and "substituted cycloalkyl" as used herein refer to an alkyl or cycloalkyl groups having one or more substituents. The substituents can include, but are not limited to, cycloalkyl, aryl, heteroaryl, heterocycloalkyl, substituted aryl, substituted heteroaryl, and substituted heterocycloalkyl. The preferred substituted alkyl groups have one to twenty carbon atoms, not including carbon atoms of the substituent group. Preferably, a substituted alkyl group is mono- or di-substituted at one, two, or three carbon atoms. The substituents can be bound to the same carbon or different carbon atoms.

The term "ester" as used herein refers to a group of the general formula:

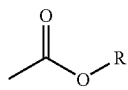

wherein R is an alkyl group, cycloalkyl group, substituted alkyl group, or a substituted cycloalkyl group.

The term "aryl" as used herein refers to monocyclic, fused bicyclic, and fused tricyclic carbocyclic aromatic ring systems including, but not limited to, phenyl, naphthyl, tetrahydronaphthyl, phenanthrenyl, biphenylenyl, indanyl, indenyl, anthracenyl, and fluorenyl.

The term "heteroaryl" as used herein refers to monocyclic, fused bicyclic, and fused tricyclic aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, and benzothiazolyl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "substituted aryl," "substituted heteroaryl," and "substituted heterocycloalkyl" as used herein refer to an aryl, heteroaryl, or heterocycloalkyl group substituted by a replacement of one, two, or three of the hydrogen atoms thereon with a substitute selected from the group consisting of halo, OR, N(R)$_2$, C(=O)N(R)$_2$, CN, alkyl, substituted alkyl, aryl, substituted aryl, heteroaryl, substituted heteroaryl, cycloalkyl, substituted cycloalkyl, heterocycloalkyl, substituted heterocycloalkyl, O(CH$_2$)$_{1-3}$N(R)$_2$, O(CH$_2$)$_{1-3}$CO$_2$H, and trifluoromethyl.

The term "amino" as used herein refers an —NH$_2$ or —NH— group, wherein each hydrogen in each formula can be replaced with an alkyl, cycloalkyl, aryl, heteroaryl, heterocycloalkyl, substituted alkyl, substituted cycloalkyl, substituted aryl, substituted heteroaryl, or substituted heterocycloalkyl group, i.e., N(R)$_2$. In the case of —NH$_2$, the hydrogen atoms also can be replaced with substituents taken together to form a 5- or 6-membered aromatic or non-aromatic ring, wherein one or two carbons of the ring optionally are replaced with a heteroatom selected from the group consisting of sulfur, oxygen, and nitrogen. The ring also optionally can be substituted with an alkyl group. Examples of rings formed by substituents taken together with the nitrogen atom include morpholinyl, phenylpiperazinyl, imidazolyl, pyrrolidinyl, (N-methyl)piperazinyl, and piperidinyl.

The term "cyano" as used herein refers to a —C≡N group, also designated —CN.

The terms "waterproof" and "waterproofing" as used herein refers to any increase in a material/surface's ability to repel water from permeating the material/surface. These terms are not intended to mean that a material/surface is completely impervious to water, rather, the terms "waterproof" and "waterproofing" are intended to be understood as making a material/surface less water permeable relative to not having been "waterproofed" or having undergone "waterproofing."

A sunscreen composition disclosed herein can include a variety of photoactive compounds, including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives;: vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

UV-A radiation (about 320 nm to about 400 nm), is recognized as contributing to causing damage, to skin particularly to very lightly-colored or sensitive skin. A sunscreen composition disclosed herein preferably includes a UV-A photoactive compound. Preferably, a sunscreen composition disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

A preferred combination of photoactive compounds in a sunscreen composition includes a UV-A and a UV-B photoactive compound. However, when 2-ethylhexyl-p-methoxycinnamate is included in a mixture with a dibenzoylmethane derivative, the dibenzoylmethane derivative can become particularly unstable. Without intending to be limited to any particular mechanism, it is believed that the cinnamate ester reacts with an excited-state dibenzoylmethane derivative in a bimolecular pathway that renders both the dibenzoylmethane derivative and the cinnamate ester incapable of absorbing UV radiation. It has been found, quite surprisingly, that the use of a polymer containing one or more crylene and/or fluorene moieties covalently bonded to the polymer backbone increases the stability of a sunscreen composition that includes 2-ethylhexyl-p-methoxycinnamate and a dibenzoylmethane derivative. Thus, one embodiment of a sunscreen composition includes 2-ethylhexyl-p-methoxycinnamate, a dibenzoylmethane derivative, and a polymer containing one or more crylene and/or fluorene moieties covalently bonded to the polymer backbone.

One embodiment of a polymer compound disclosed herein is a compound of formula (I):

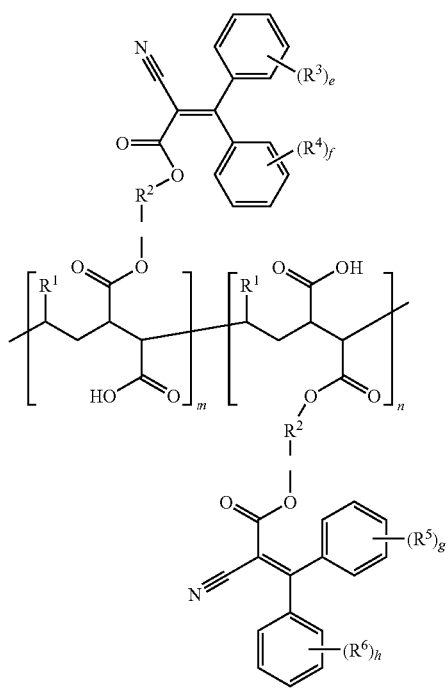

(I)

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1. Preferably, $R^1$ and $R^2$ are selected from the group consisting of $C_1$-$C_{30}$ alkyl groups. More preferably, $R^1$ is a $C_{16}$ straight chain alkyl group, and $R^2$ is a 2,2-dimethylpropyl group.

Another embodiment of a polymer compound disclosed herein is a compound of formula (II):

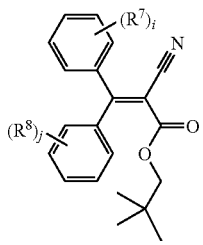

(II)

-continued

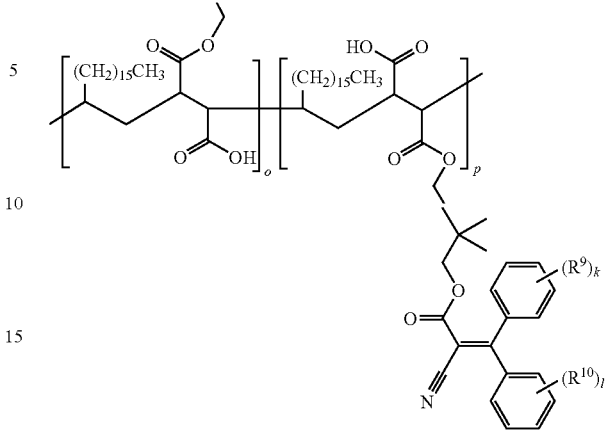

wherein $R^7$, $R^8$, $R^9$, and $R^{10}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, i, j, k, and l are each in the range of 0 to 4, o and p are each in the range of 0 to 5000, and the sum of o plus p is at least 1. Compound of formula (II) are also referred to herein as Octadecene/Crylene maleate copolymer.

Another embodiment of a polymer compound disclosed herein is the product of the reaction between the polymer of formula (III) and a compound selected from the group consisting of compounds of formulae (IV), (V), and combinations thereof:

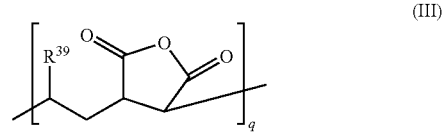

(III)

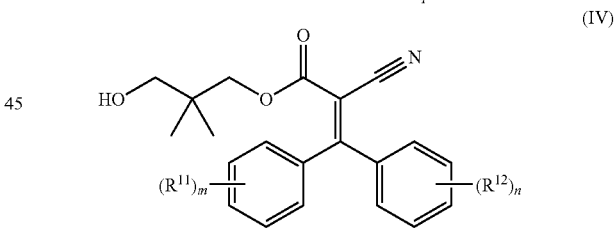

(IV)

(V)

wherein $R^{11}$, $R^{12}$, $R^{13}$, $R^{14}$, and $R^{39}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, m, n, o, and p are each in the range of 0 to 4, and q is in the range of 2 to 5000. Preferably, $R^{39}$ is selected from the group consisting of $C_1$-$C_{30}$ alkyl groups. More preferably, $R^{39}$ is a $C_{16}$ straight chain alkyl group.

Compounds of formula (I), quite surprisingly, are able to increase the stability of a photoactive compound in a sunscreen composition. Accordingly, another embodiment is a sunscreen composition sunscreen composition, including a mixture of a photoactive compound, and a compound of formula (I):

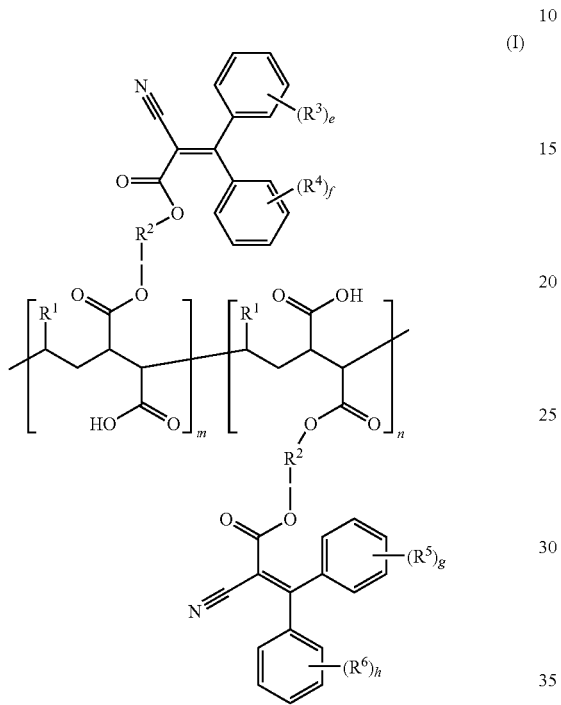

(I)

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1. Preferably, $R^1$ and $R^2$ are selected from the group consisting of $C_1$-$C_{30}$ alkyl groups. More preferably, $R^1$ is a $C_{16}$ straight chain alkyl group, and $R^2$ is a 2,2-dimethylpropyl group. Preferably, a compound of formula (I) is present in a sunscreen composition in a range of about 0.01% to about 30% by weight of the total weight of the composition, more preferably in a range of about 0.1% to about 10%.

Figure 2:
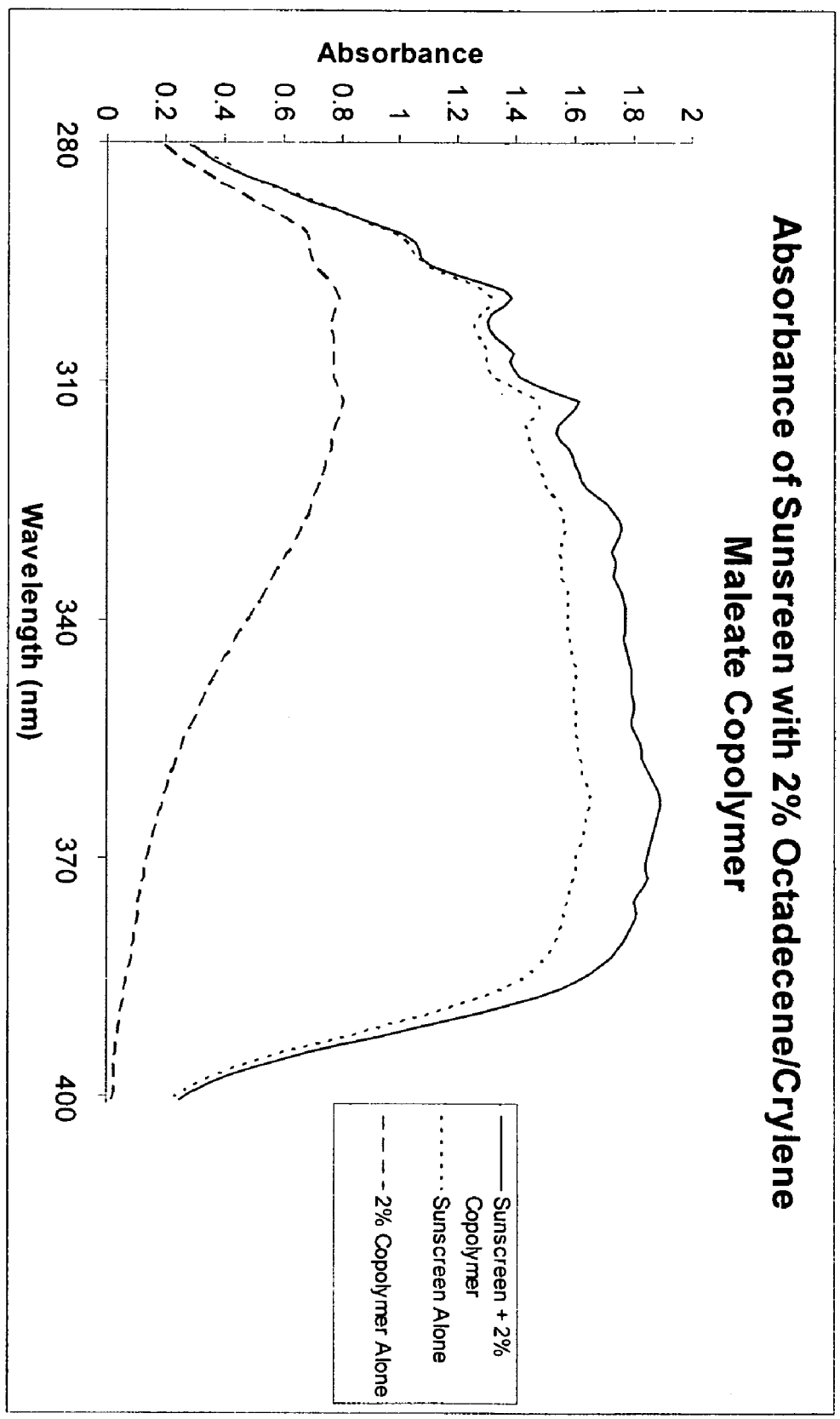
FIG. 2 is a graph of the absorbance of a sunscreens composition that includes 2% Octadecene/Crylene maleate copolymer as the only UV-absorbing compound, a sunscreen composition (with UV-absorbing compounds) that does not include Octadecene/Crylene maleate copolymer, and a sunscreen composition including 2% of the Octadecene/Crylene maleate copolymer and other UV-absorbing compounds, from a wavelength of 280 nm to 400 nm.

Compounds of formula (I), quite surprisingly, are able to absorb UV-radiation and to increase the photostability of a photoactive compound in a sunscreen composition, the compounds of formula (I) are therefore able to be used to protect skin from the harmful effects of UV-radiation. FIG. 1 shows the absorbance spectra from 280 nm to 400 nm for a sunscreen composition wherein Octadecene/Crylene maleate copolymer (a compound of formula (I) wherein $R^1$ is a $C_{16}$ straight chain alkyl group, $R^2$ is a 2,2-dimethylpropyl group, and there is no substitution of the aromatic rings of the crylene moieties) is present as the only UV-absorbing compound. FIG. 2 is a graph of the absorbance spectra from 280 nm to 400 nm for the sunscreen compositions shown in Table III, and the composition shown in Table II, wherein Octadecene/Crylene maleate copolymer is included as the only UV-absorbing compound. FIG. 2 confirms that Octadecene/Crylene maleate copolymer absorbs UV-radiation independent of other UV-absorbing agents that may be present in a sunscreen composition. Accordingly, another embodiment is a method of protecting human skin from ultraviolet radiation, including topically applying to the skin, in a cosmetically acceptable carrier, a compound of formula (I):

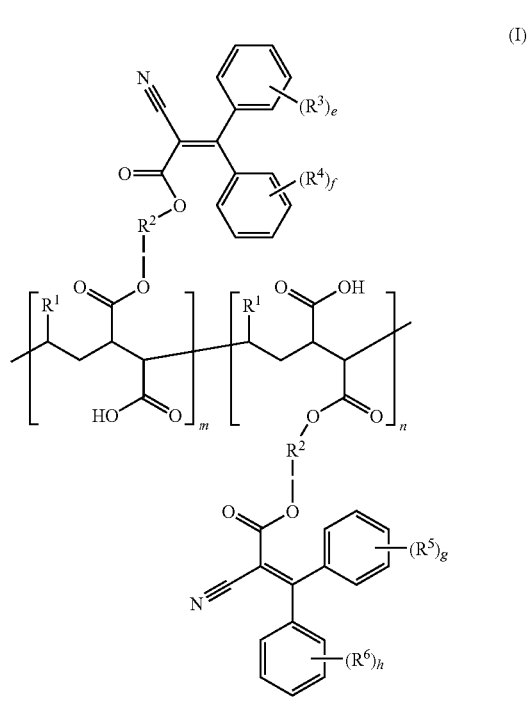

(I)

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1. Preferably, $R^1$ and $R^2$ are selected from the group consisting of $C_1$-$C_{30}$ alkyl groups. More preferably, $R^1$ is a $C_{16}$ straight chain alkyl group, and $R^2$ is a 2,2-dimethylpropyl group. Preferably, a compound of formula (I) is present in a sunscreen composition in a range of about 0.01% to about 30% by weight of the total weight of the composition, more preferably in a range of about 0.1% to about 10%.

It has been found that a polymer compound of formula (I) may be used to waterproof a surface, and thereby, make the surface less water permeable. This aspect of a compound of formula (I) may be used in a variety of applications, including a sunscreen composition. A compound of formula (I) may be added to a sunscreen composition to help prevent the loss of the composition that may accompany the immersion in water of the object (e.g., human skin) that has been applied with the composition. Accordingly, another embodiment is a method of waterproofing a surface, including applying a compound of formula (I) to a selected area of the surface:

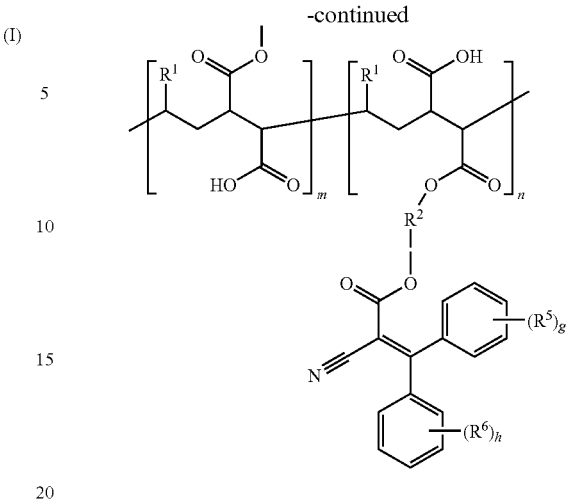

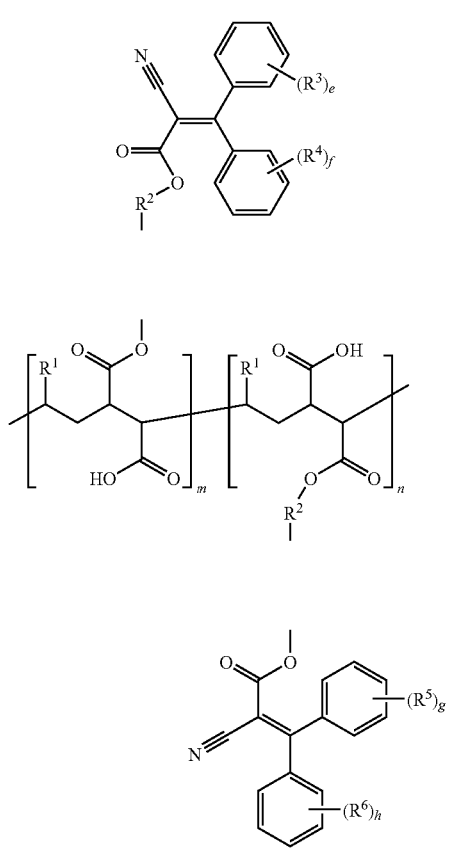

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1. Preferably, $R^1$ and $R^2$ are selected from the group consisting of $C_1$-$C_{30}$ alkyl groups. More preferably, $R^1$ is a $C_{16}$ straight chain alkyl group, and $R^2$ is a 2,2-dimethylpropyl group.

It has also been found that a polymer compound of formula (I) may be used to form a film on a surface, and when added to a composition, a compound of formula (I) may provide film-forming properties to the composition. Accordingly, another embodiment is a method for forming a film over at least part of a surface, including spreading a compound of formula (I) on the part of the surface:

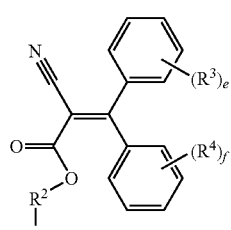

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1. Preferably, $R^1$ and $R^2$ are selected from the group consisting of $C_1$-$C_{30}$ alkyl groups. More preferably, $R^1$ is a $C_{16}$ straight chain alkyl group, and $R^2$ is a 2,2-dimethylpropyl group.

Likewise, a compound of formula (I), quite surprisingly, is able to increase the photostability of a dibenzoylmethane derivative. Without intending to be limited to a particular mechanism, it is believed that a compound selected from the group consisting of compounds of formula (I) are able to photostabilize a dibenzoylmethane derivative by accepting the triplet excited energy from an excited dibenzoylmethane derivative. Thus, another embodiment of the compounds, compositions, and methods disclosed herein is to provide a method of photostabilizing a dibenzoylmethane derivative, the method including the step of, adding to the dibenzoylmethane derivative a photostabilizing amount of a compound of formula (I):

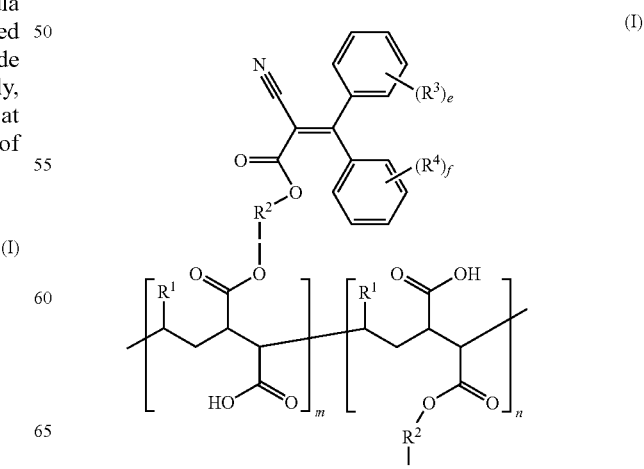

-continued

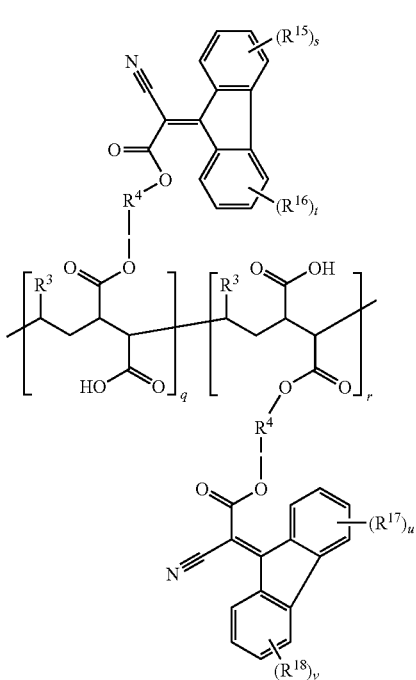

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1. Preferably, $R^1$ and $R^2$ are selected from the group consisting of $C_1C_{-30}$ alkyl groups. More preferably, $R^1$ is a $C_{16}$ straight chain alkyl group, and $R^2$ is a 2,2-dimethylpropyl group.

Yet another embodiment of a polymer compound disclosed herein is a compound of formula (VI):

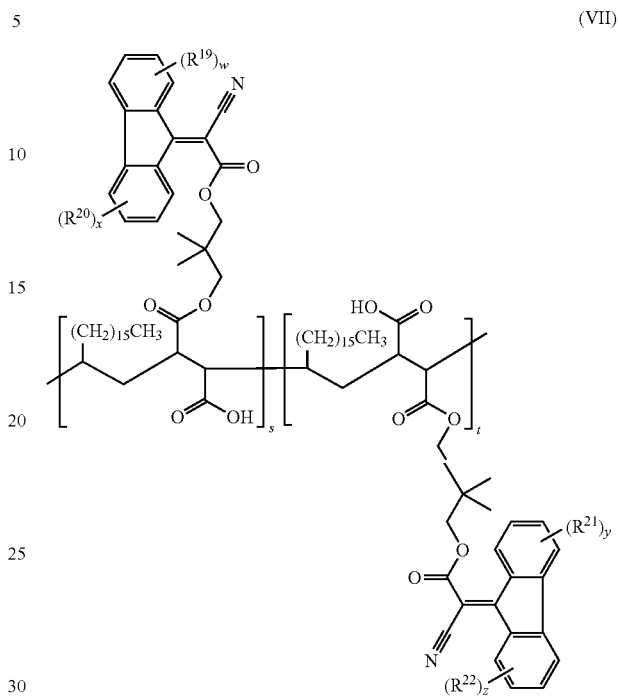

wherein $R^3$, $R^4$, $R^{15}$, $R^{16}$, $R^{17}$, and $R^{18}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, s, t, u, and v are each in the range of 0 to 4, q and r are each in the range of 0 to 5000, and the sum of q plus r is at least 1. Preferably, $R^3$ and $R^4$ are selected from the group consisting of $C_1$-$C_{30}$ alkyl groups. More preferably, $R^3$ is a $C_{16}$ straight chain alkyl group, and $R^4$ is a 2,2-dimethylpropyl group.

Another embodiment of a polymer compound disclosed herein is a compound of formula (VII):

(VII)

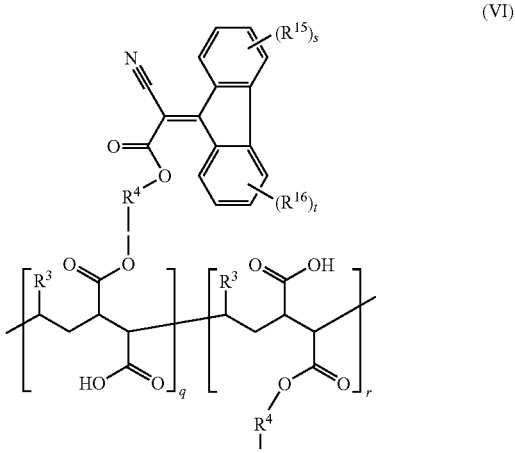

wherein $R^{19}$, $R^{20}$, $R^{21}$, and $R^{22}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, w, x, y, and z are each in the range of 0 to 4, s and t are each in the range of 0 to 5000, and the sum of s plus t is at least 1.

Compounds of formula (VI), quite surprisingly, are able to increase the stability of a photoactive compound in a sunscreen composition. Accordingly, another embodiment is a sunscreen composition sunscreen composition, including a mixture of a photoactive compound, and a compound of formula (VI):

(VI)

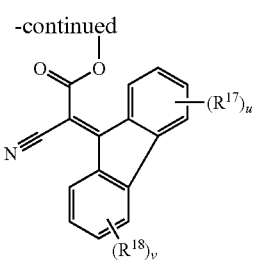

wherein $R^3$, $R^4$, $R^{15}$, $R^{16}$, $R^{17}$, and $R^{18}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, s, t, u, and v are each in the range of 0 to 4, q and r are each in the range of 0 to 5000, and the sum of q plus r is at least 1. Preferably, $R^3$ and $R^4$ are selected from the group consisting of $C_1$-$C_{30}$ alkyl groups. More preferably, $R^3$ is a $C_{16}$ straight chain alkyl group, and $R^4$ is a 2,2-dimethylpropyl group. Preferably, a compound of formula (VI) is present in a sunscreen composition in a range of about 0.01% to about 30% by weight of the total weight of the composition, more preferably in a range of about 0.1% to about 10%.

Compounds of formula (VI), quite surprisingly, are able to absorb UV-radiation and to increase the photostability of a photoactive compound in a sunscreen composition, the compounds of formula (VI) are therefore able to be used to protect skin from the harmful effects of UV-radiation. Accordingly, another embodiment is a method of protecting human skin from ultraviolet radiation, including topically applying to the skin, in a cosmetically acceptable carrier, a compound of formula (VI):

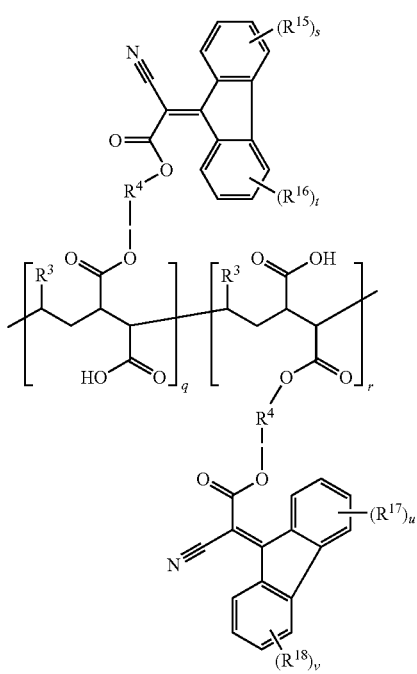

(VI)

wherein $R^3$, $R^4$, $R^{15}$, $R^{16}$, $R^{17}$, and $R^{18}$ are the same or different and selected from the group consisting of $C_1$-$C_{30}$ alkyl, $C_1$-$C_{30}$ substituted alkyl $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, s, t, u, and v are each in the range of 0 to 4, q and r are each in the range of 0 to 5000, and the sum of q plus r is at least 1. Preferably, $R^3$ and $R^4$ are selected from the group consisting of $C_1$-$C_{30}$ alkyl groups. More preferably, $R^3$ is a $C_{16}$ straight chain alkyl group, and $R^4$ is a 2,2-dimethylpropyl group. Preferably, a compound of formula (VI) is present in a sunscreen composition in a range of about 0.01% to about 30% by weight of the total weight of the composition, more preferably in a range of about 0.1% to about 10%.

It has been found that a polymer compound of formula (VI) may be used to waterproof a surface, and thereby, make the surface less water permeable. This aspect of a compound of formula (VI) may be used in a variety of applications, including a sunscreen composition. A compound of formula (VI) may be added to a sunscreen composition to help prevent the loss of the composition that may accompany the immersion in water of the object (e.g., human skin) that has been applied with the composition. Accordingly, another embodiment is a method of waterproofing a surface, including applying a compound of formula (VI) to a selected area of the surface:

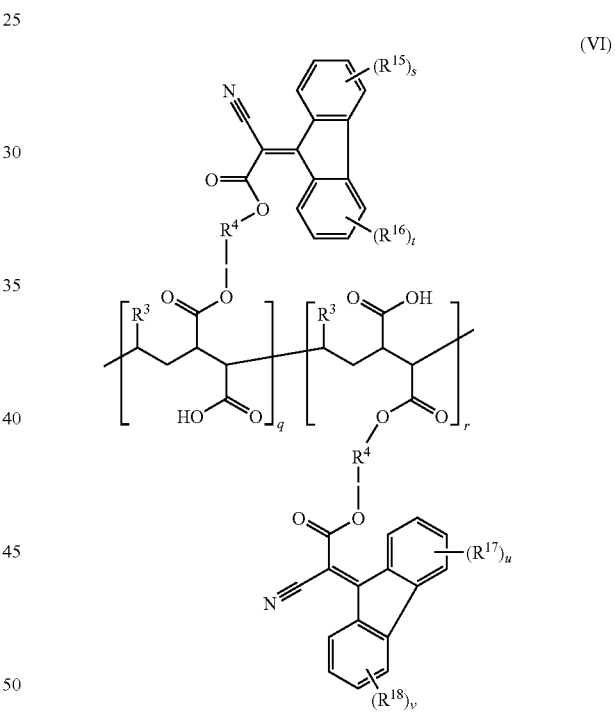

(VI)

wherein $R^3$, $R^4$, $R^{15}$, $R^{16}$, $R^{17}$, and $R^{18}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, s, t, u, and v are each in the range of 0 to 4, q and r are each in the range of 0 to 5000, and the sum of q plus r is at least 1. Preferably, $R^3$ and $R^4$ are selected from the group consisting of $C_1$-$C_{30}$ alkyl groups. More preferably, $R^3$ is a $C_{16}$ straight chain alkyl group, and $R^4$ is a 2,2-dimethylpropyl group.

It has also been found that a polymer compound of formula (VI) may be used to form a film on a surface, and when added to a composition, a compound of formula (VI) may provide film-forming properties to the composition. Accordingly, another embodiment is a method for forming a film over at least part of a surface, including spreading a compound of formula (VI) on the part of the surface:

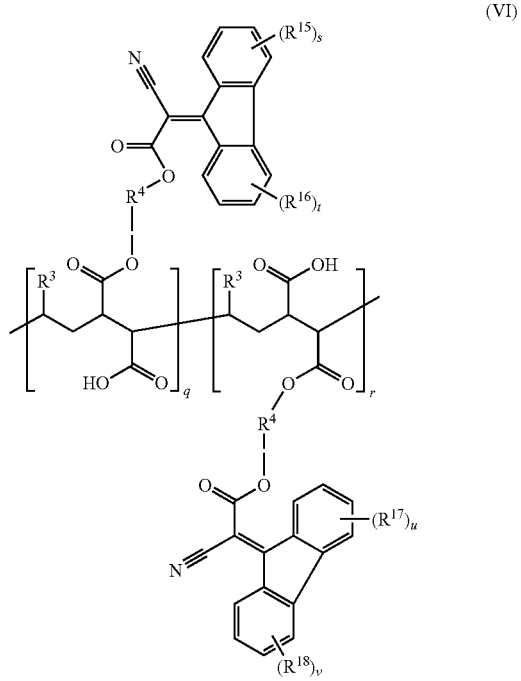

(VI)

wherein $R^3$, $R^4$, $R^{15}$, $R^{16}$, $R^{17}$, and $R^{18}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, s, t, u, and v are each in the range of 0 to 4, q and r are each in the range of 0 to 5000, and the sum of q plus r is at least 1. Preferably, $R^3$ and $R^4$ are selected from the group consisting of $C_1$-$C_{30}$ alkyl groups. More preferably, $R^3$ is a $C_{16}$ straight chain alkyl group, and $R^4$ is a 2,2-dimethylpropyl group.

Likewise, a compound of formulae (VI), quite surprisingly, is able to increase the photostability of a dibenzoylmethane derivative. Without intending to be limited to a particular mechanism, it is believed that a compound selected from the group consisting of compounds of formula (VI) are able to photostabilize a dibenzoylmethane derivative by accepting the triplet excited energy from an excited dibenzoylmethane derivative. Thus, another embodiment of the compounds, compositions, and methods disclosed herein is a method of photostabilizing a dibenzoylmethane derivative, the method including the step of, adding to the dibenzoylmethane derivative a photostabilizing amount of a compound of formula (VI):

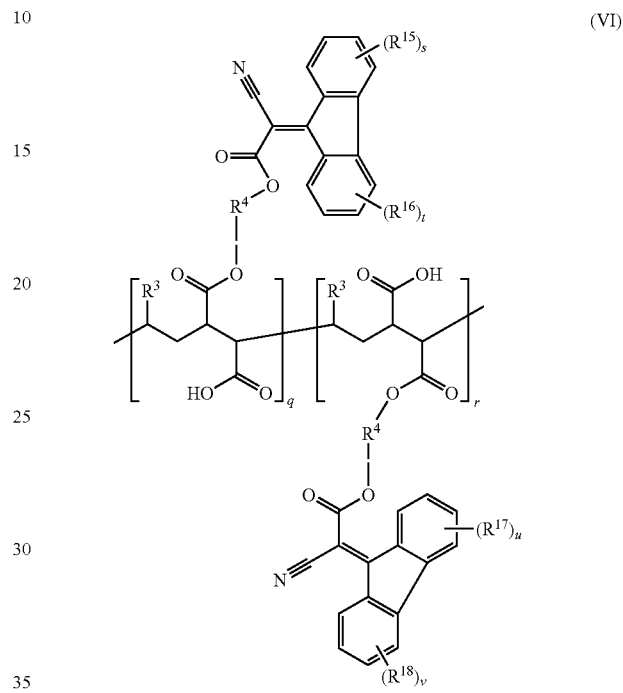

(VI)

wherein $R^3$, $R^4$, $R^{15}$, $R^{16}$, $R^{17}$, and $R^{18}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, s, t, u, and v are each in the range of 0 to 4, q and r are each in the range of 0 to 5000, and the sum of q plus r is at least 1. Preferably, $R^3$ and $R^4$ are selected from the group consisting of $C_1$-$C_{30}$ alkyl groups: More preferably, $R^3$ is a $C_{16}$ straight chain alkyl group, and $R^4$ is a 2,2-dimethylpropyl group.

Yet another embodiment of a polymer compound disclosed herein is a compound of formula (IX):

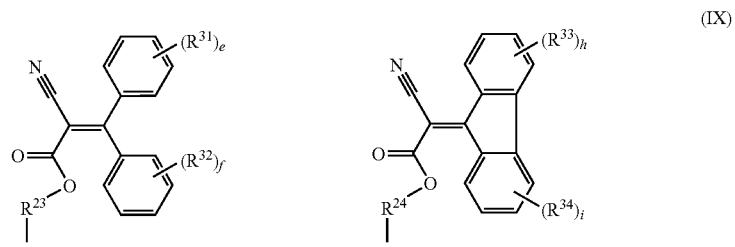

(IX)

-continued

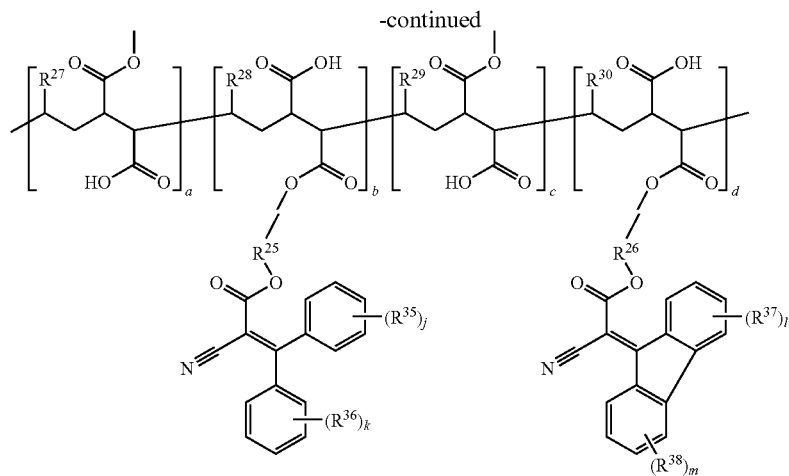

wherein $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, f, h, i, j, k, l, and m are each in the range of 0 to 4, a, b, c, and d are each in the range of 0 to 5000, and the sum of a, b, c, and d is at least 1. Preferably, $R^{23}$, $R^{24}$, $R^{25}$, $R^{26}$, $R^{27}$, $R^{28}$, $R^{29}$, and $R^{30}$ are selected from the group consisting of $C_1$-$C_{30}$ alkyl groups. More preferably, $R^{23}$, $R^{24}$, $R^{254}$, $R^{26}$ are $C_{16}$ straight chain alkyl groups, and $R^{27}$, $R^{28}$, $R^{29}$, and $R^{30}$ are 2,2-dimethylpropyl groups.

Another embodiment of a polymer compound disclosed herein is a compound of formula (X):

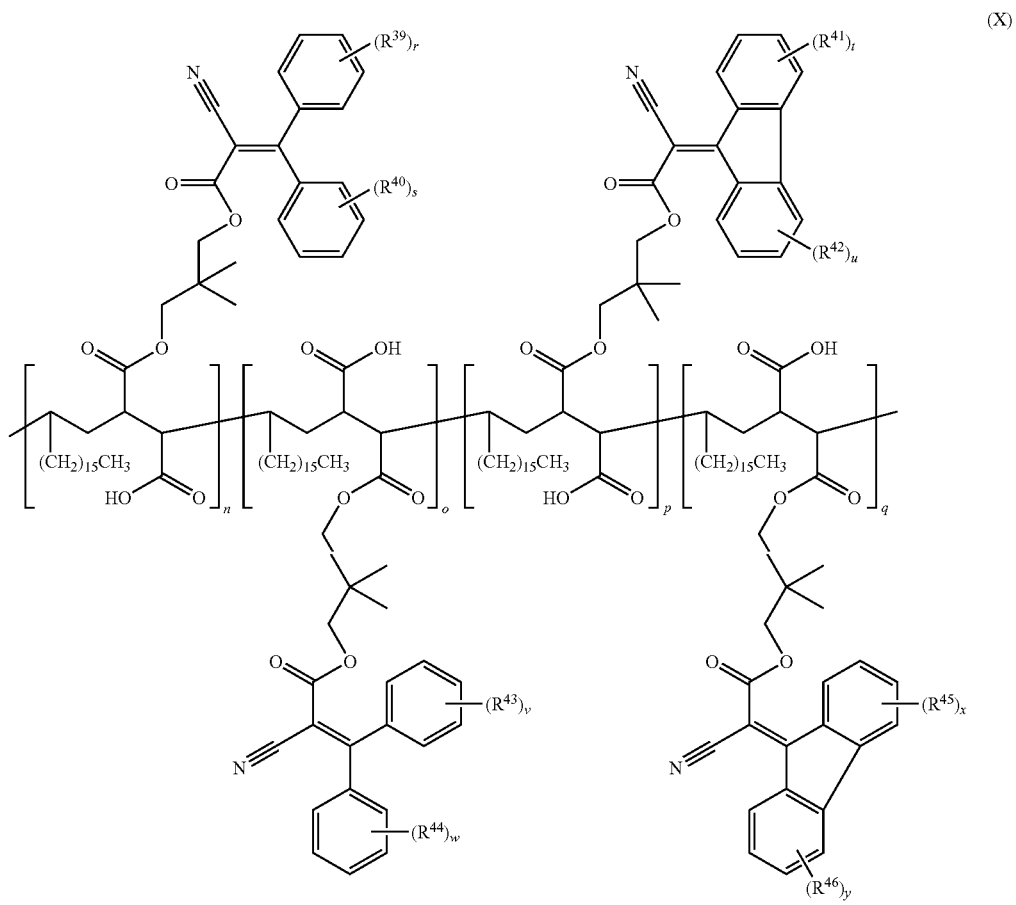

wherein $R^{39}$, $R^{40}$, $R^{41}$, $R^{42}$, $R^{43}$, $R^{44}$, $R^{45}$, and $R^{46}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, r, s, t, u, v, w, x, and y are each in the range of 0 to 4, n, o, p, and q are each in the range of 0 to 5000, and the sum of n, o, p, and q is at least 1.

Compounds of formula (IX), quite surprisingly, are able to increase the stability of a photoactive compound in a sunscreen composition. Accordingly, another embodiment is a sunscreen composition sunscreen composition, including a mixture of a photoactive compound, and a compound of formula (IX):

cloalkyl, cyano, and amino, e, f, h, i, j, k, l, and m are each in the range of 0 to 4, a, b, c, and d are each in the range of 0 to 5000, and the sum of a, b, c, and d is at least 1. Preferably, $R^{23}$, $R^{24}$, $R^{25}$, $R^{26}$, $R^{27}$, $R^{28}$, $R^{29}$, and $R^{30}$ are selected from the group consisting of $C_1$-$C_{30}$ alkyl groups. More preferably, $R^{23}$, $R^{24}$, $R^{25}$, $R^{26}$ are $C_{16}$ straight chain alkyl groups, and $R^{27}$, $R^{28}$, $R^{29}$, and $R^{30}$ are 2,2-dimethylpropyl groups. Preferably, a compound of formula (IX) is present in a sunscreen composition in a range of about 0.01% to about 30% by weight of the total weight of the composition, more preferably in a range of about 0.1% to about 10%.

Compounds of formula (IX), quite surprisingly, are able to absorb UV-radiation and to increase the photostability of a photoactive compound in a sunscreen composition, the com-

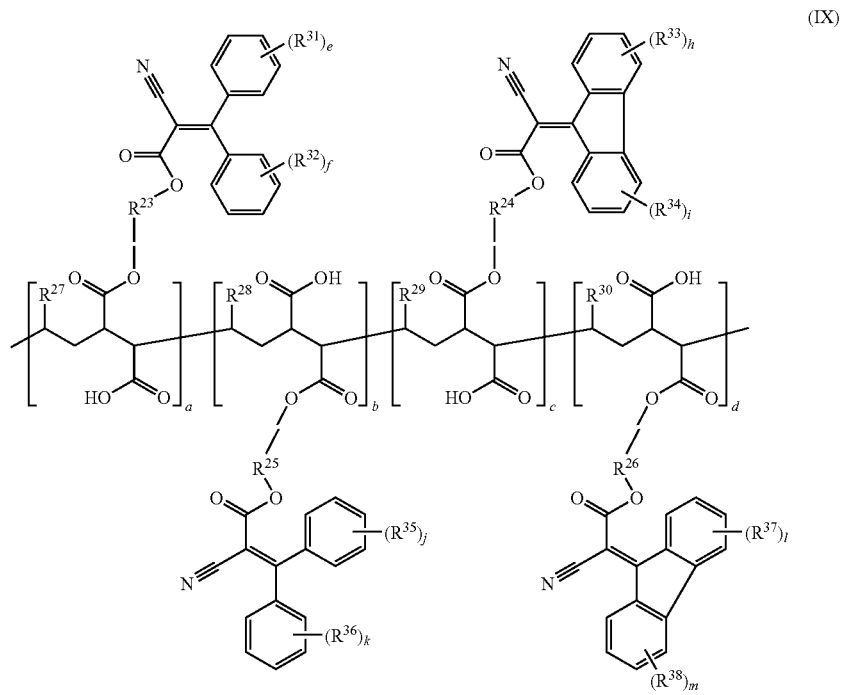

(IX)

wherein $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocypounds of formula (IX) are therefore able to be used to protect skin from the harmful effects of UV-radiation. Accordingly, another embodiment is a method of protecting human skin from ultraviolet radiation, including topically applying to the skin, in a cosmetically acceptable carrier, a compound of formula (IX):

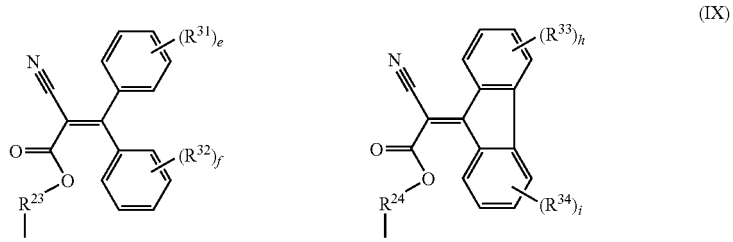

(IX)

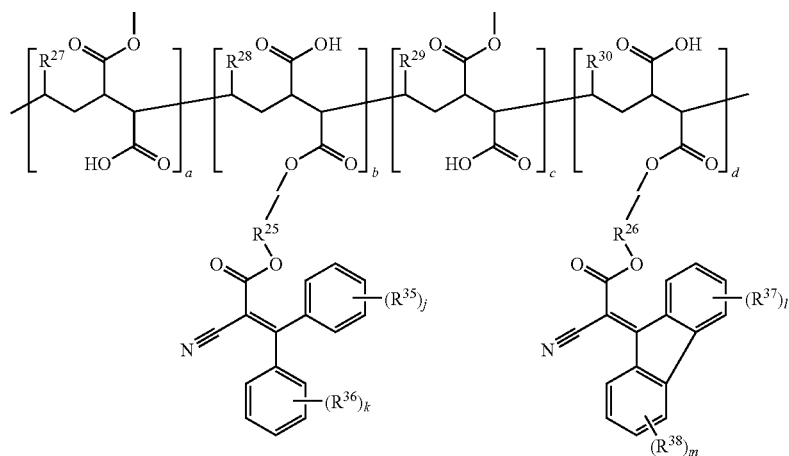

wherein $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, f, h, i, j, k, l, and m are each in the range of 0 to 4, a, b, c, and d are each in the range of 0 to 5000, and the sum of a, b, c, and d is at least 1. Preferably, $R^{23}$, $R^{24}$, $R^{25}$, $R^{26}$, $R^{27}$, $R^{28}$, $R^{29}$, and $R^{30}$ are selected from the group consisting of $C_1$-$C_{30}$ alkyl groups. More preferably, $R^{23}$, $R^{24}$, $R^{25}$, $R^{26}$ are $C_{16}$ straight chain alkyl groups, and $R^{27}$, $R^{28}$, $R^{29}$, and $R^{30}$ are 2,2-dimethylpropyl groups. Preferably, a compound of formula (IX) is present in a sunscreen composition in a range of about 0.01% to about 30% by weight of the total weight of the composition, more preferably in a range of about 0.1% to about 10%.

It has been found that a polymer compound of formula (IX) may be used to waterproof a surface, and thereby, make the surface less water permeable. This aspect of a compound of formula (IX) may be used in a variety of applications, including a sunscreen composition. A compound of formula (IX) may be added to a sunscreen composition to help prevent the loss of the composition that may accompany the immersion in water of the object (e.g., human skin) that has been applied with the composition. Accordingly, another embodiment is a method of waterproofing a surface, including applying a compound of formula (IX) to a selected area of the surface:

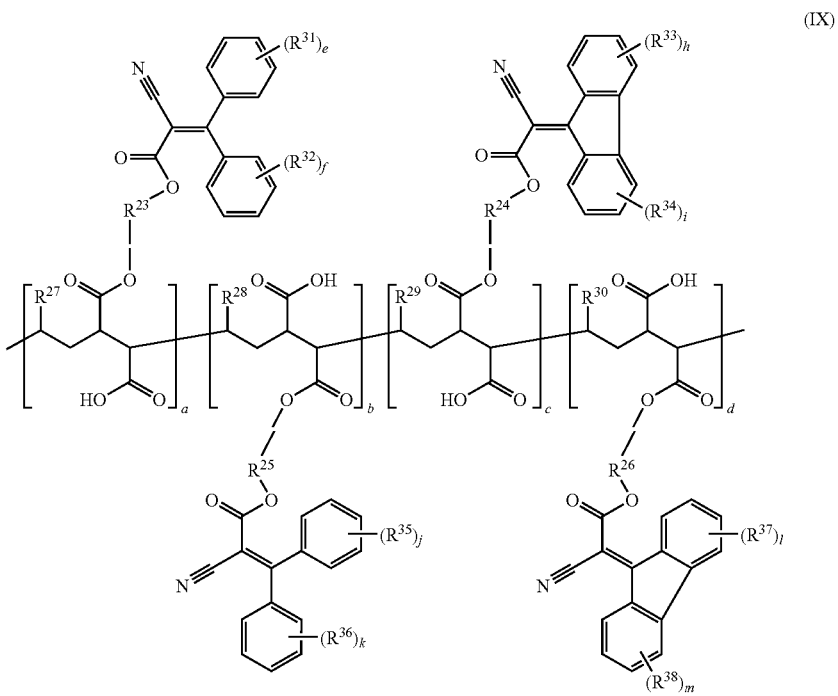

wherein $R^{23}$, $R^{24}$, $R^{25}$, $R^{26}$, $R^{27}$, $R^{28}$, $R^{29}$, $R^{30}$, $R^{32}$, $R^{33}$, $R^{34}$, $R^{35}$, $R^{36}$, $R^{37}$, and $R^{38}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, f, h, i, j, k, l, and m are each in the range of 0 to 4, a, b, c, and d are each in the range of 0 to 5000, and the sum of a, b, c, and d is at least 1. Preferably $R^{23}$, $R^{24}$, $R^{25}$, $R^{26}$, $R^{27}$, $R^{28}$, $R^{29}$, and $R^{30}$ are selected from the group consisting of $C_1$-$C_{30}$ alkyl groups. More preferably, $R^{23}$, $R^{24}$, $R^{25}$, $R^{26}$ are $C_{16}$ straight chain alkyl groups, and $R^{27}$, $R^{28}$, $R^{29}$, and $R^{30}$ are 2,2-dimethylpropyl groups.

It has also been found that a polymer compound of formula (IX) may be used to form a film on a surface, and when added to a composition, a compound of formula (IX) may provide film-forming properties to the composition. Accordingly, another embodiment is a method for forming a film over at least part of a surface, including spreading a compound of formula (IX) on the part of the surface:

substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, f, h, i, j, k, l, and m are each in the range of 0 to 4, a, b, c, and d are each in the range of 0 to 5000, and the sum of a, b, c, and d is at least 1. Preferably, $R^{23}$, $R^{24}$, $R^{25}$, $R^{26}$, $R^{27}$, $R^{28}$, $R^{29}$, and $R^{30}$ are selected from the group consisting of $C_1$-$C_{30}$ alkyl groups. More preferably, $R^{23}$, $R^{24}$, $R^{25}$, $R^{26}$ are $C_{16}$ straight chain alkyl groups, and $R^{27}$, $R^{28}$, $R^{29}$, and $R^{30}$ are 2,2-dimethylpropyl groups.

Likewise, a compound of formulae (IX), quite surprisingly, is able to increase the photostability of a dibenzoylmethane derivative. Without intending to be limited to a particular mechanism, it is believed that a compound selected from the group consisting of compounds of formula (IX) are able to photostabilize a dibenzoylmethane derivative by accepting the triplet excited energy from an excited dibenzoylmethane derivative. Thus, another embodiment of the compounds, compositions, and methods disclosed herein is a method of photostabilizing a dibenzoylmethane derivative, the method

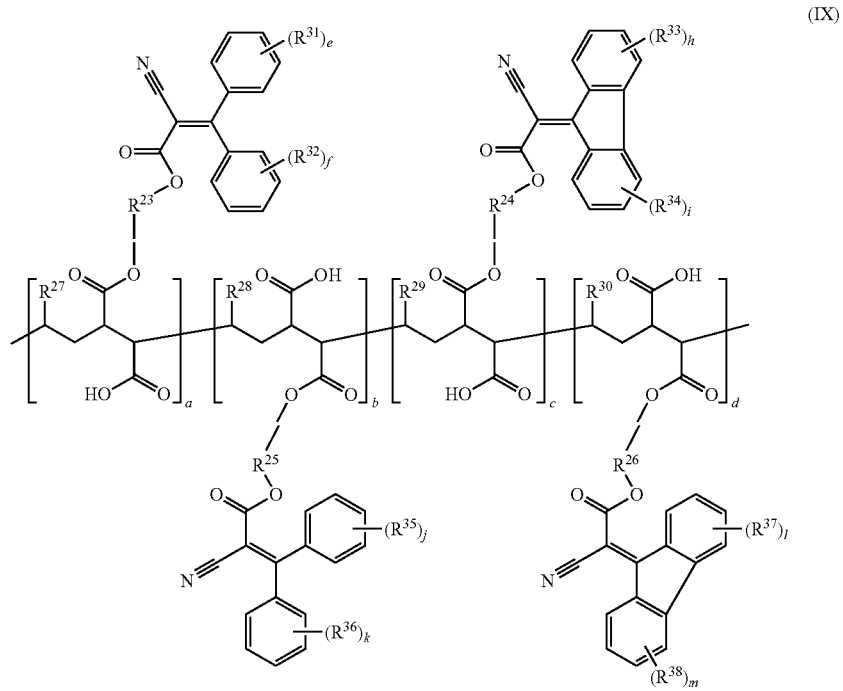
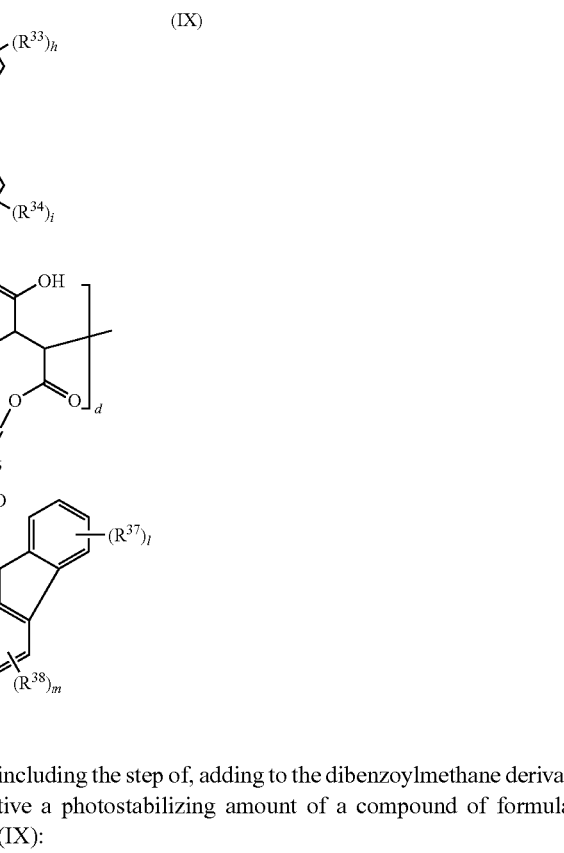

(IX)

wherein $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$ are the same or different and selected from the group consisting of $C_1$-$C_{30}$ alkyl, $C_1$-$C_{30}$ including the step of, adding to the dibenzoylmethane derivative a photostabilizing amount of a compound of formula (IX):

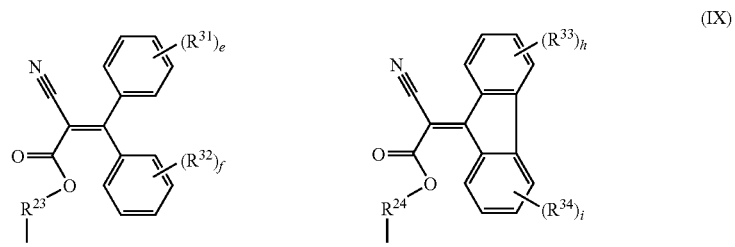

(IX)

-continued

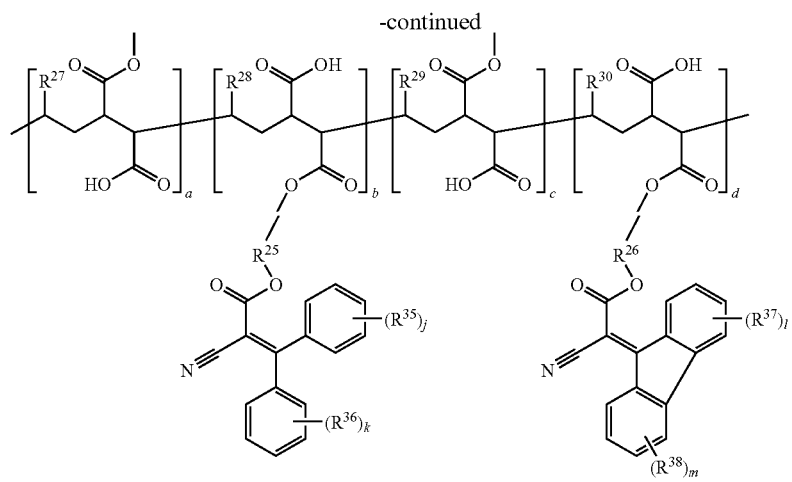

wherein $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{35}$, $R^{36}$, $R^{37}$, and $R^{38}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, f, h, i, j, k, l, and m are each in the range of 0 to 4, a, b, c, and d are each in the range of 0 to 5000, and the sum of a, b, c, and d is at least 1. Preferably, $R^{23}$, $R^{24}$, $R^{25}$, $R^{26}$, $R^{27}$, $R^{28}$, $R^{29}$, and $R^{30}$ are selected from the group consisting of $C_1$-$C_{30}$ alkyl groups. More preferably, $R^{23}$, $R^{24}$, $R^{25}$, $R^{26}$ are $C_{16}$ straight chain alkyl groups, and $R^{27}$, $R^{28}$, $R^{29}$, and $R^{30}$ are 2,2-dimethylpropyl groups.

EXAMPLES

The following examples are provided to illustrate the compounds, compositions, and methods disclosed herein but are not intended to limit the scope of the compounds, compositions, and methods disclosed herein.

Example 1

The following is a preparation for a polymer compound containing crylene moieties attached to the polymer backbone, wherein Poly(octadecene-1-co-maleic anhydride) resin (PA-18 available from Chevron Chemicals Co., San Francisco, Calif.) served as a polymer starting material, and 2,2-dimethyl-3-hydroxypropyl-2-cyano-3,3-diphenylpropenoate served as the crylene moiety with a tether of neopentyl glycol. The PA-18 Polyanhydride Resin (300 g) and 2,2-dimethyl-3-hydroxypropyl-2-cyano-3,3-diphenylpropenoate (258 g) were placed in 2L 3-neck round-bottom flask and 800 ml of toluene was added. The reaction mixture was then heated and refluxed for two hours until reaction was completed (as determined by GPC). The product in solution was placed in evaporation vessels to remove the solvent. The final product was then dried and ground to give off-white powder (510 g, 91% yield).

Example 2

A composition which included only the Octadecene/Crylene maleate copolymer as the only UV-Absorbing compound by mixing the ingredients shown in Table II below:

TABLE II

| Phase | Ingredient | Weight Percent |
|---|---|---|
| A | Caprylic/capric triglycerides | 8.00% |
| | Polyisobutene | 3.00% |
| | Phenylethyl benzoate | 1.00% |
| | Diethylhexyl malate | 2.00% |
| B | Octadecene/Crylene maleate copolymer | 2.00% |
| C | Stearyl alcohol | 1.00% |
| | Steareth-21 | 0.22% |
| | Steareth-2 | 0.28% |
| | Polyglyceryl-3 methyl glucose distearate | 3.00% |
| D | Dimethicone (100 cSt) | 0.40% |
| E | Water | 72.56% |
| | Disodium EDTA | 0.05% |
| | Carbomer | 0.20% |
| F | Sorbitol (70%) | 4.29% |
| | Phenoxyethanol, Methylparaben, Ethylparaben, Propylparaben, and Isobutylparaben | 1.00% |
| | Triethanolamine | 1.00% |

An oil-in-water emulsion was created, wherein the aqueous phase included a mixture of the ingredients in Phase E, and the oil phase included a mixture of the ingredients of Phases A, B, C, and D. The emulsion was prepared by combining the ingredients of Phase A, and adding this mixture of ingredients to a vessel, and heating the vessel to about 90° C. The ingredients from Phases B, C, and D were then added to the heated vessel with stirring until the mixture became clear and homogeneous. In another vessel, the ingredients of Phase E were added in the order shown in Table II, with continuous stirring. The vessel containing the ingredients of Phase E was then heated to about 80° C. With homogenization, the contents of the vessel containing the oil phase (a mixture of the ingredients of Phases A, B, C, and D) were added to the vessel containing the water phase (a mixture of the ingredients of Phase E). The resulting mixture was homogenized for three minutes, and then the vessel was remove from heat source and allowed to cool. When the temperature of the mixture fell below 40° C., the ingredients of Phase F were added. The mixture was stirred until a smooth cream was formed. The resulting cream was then packaged to avoid the inadvertent photodegradation of the UV-absorbing compounds in the composition.

FIG. 1 is a graph of the percent absorbance of the sunscreen composition listed in Table II. As shown in FIG. 1, the Octadecene/Crylene maleate copolymer absorbs over the entire UV-spectrum, but achieves its maximum absorbance in the range of about 290-330 nm.

Example 3

Two sunscreen compositions were prepared by mixing the ingredients shown in Table III below:

TABLE III

| Phase | Ingredient | Sunscreen w/0% Polymer (wt. %) | Sunscreen w/2% Polymer (wt. %) |
|---|---|---|---|
| A | Octyl salicylate | 5.00% | 5.00% |
| | Homosalate | 7.50% | 7.50% |
| | Diethylhexyl 2,6-naphthalate | 2.50% | 2.50% |
| | Octocrylene | 2.50% | 2.50% |
| | Dimethyl capramide | 1.00% | 1.00% |
| | Diethylhexyl malate | 2.01% | 2.01% |
| B | Avobenzone | 3.00% | 3.00% |
| | Benzophenone-3 | 0.49% | 0.49% |
| C | Octyldodecanol | 2.00% | |
| | Octadecene/Crylene maleate copolymer | | 2.00% |
| D | Stearyl alcohol | 1.00% | 1.00% |
| | Steareth 21 | 0.29% | 0.29% |
| | Steareth 2 | 0.21% | 0.21% |
| | Polyglyceryl-3 methyl glucose distearate | 3.00% | 3.00% |
| E | Water | 64.16% | 63.16% |
| | Disodium EDTA | 0.05% | 0.05% |
| | Carbomer | 0.20% | 0.20% |
| | Sorbitol (70%) | 4.29% | 4.29% |
| | Phenoxyethanol, Methylparaben, Ethylparaben, Propylparaben, and Isobutylparaben | 0.60% | 0.60% |
| F | Triethanolamine | 0.2% | 1.2% |

Oil-in-water emulsions were created, wherein the aqueous phase included a mixture of the ingredients in Phase E, and the oil phase included a mixture of the ingredients of Phases A, B, C, and D. The emulsions were prepared by combining the ingredients of Phase A, and adding this mixture of ingredients to a vessel, and heating the vessel to about 90° C. The ingredients from Phases B, C, and D were then added to the heated vessel with stirring until the mixture became clear and homogeneous. In another vessel, the ingredients of Phase E were added in the order shown in Table III, with continuous stirring. The vessel containing the ingredients of Phase E was then heated to about 80° C. With homogenization, the contents of the vessel containing the oil phase (a mixture of the ingredients of Phases A, B, C, and D) to the vessel containing the water phase (a mixture of the ingredients of Phase E). The resulting mixture was homogenized for three minutes, and then the vessel was remove from heat source and allowed to cool. When temperature of the mixture fell below 40° C., the ingredient of Phase F (triethanolamine) was added. The mixture was stirred until a smooth cream was formed. The resulting creams were packaged to avoid the inadvertent photodegradation of the UV-absorbing compounds, and the creams were then used to test the photostability of the compositions.

The resulting sunscreens were tested for photostability by measuring absorbance on a Labsphere UV-1000S Ultraviolet Transmittance Analyzer (software version 1.27) before and after irradiation with a Solar Light Company model 16S solar simulator (equipped with a UG11 filter to block radiation greater than 400 nm, WG320 filter that transmits UV-radiation greater than 290 nm), and a removable WG335 filter that transmits UV-radiation greater than 320 nm). Output was monitored by a PMA 2105 UV-B DCS Detector (biologically weighted) or a PMA 2114 UV-A Detector and controlled by a PMA 2100 Automatic Dose Controller (available from Solar Light Co.).

To test stability, a synthetic skin substrate was used for testing the sunscreen compositions (VITRO-SKIN substrate (Lot No. 3059) by IMS, Inc. of Milford, Conn.). To prepare the substrate, a 300 g solution of 18 wt. % glycerin and 82 wt. % deionized water was added to a hydrating chamber (IMS), and a sheet of VITRO-SKIN was placed in the hydrating chamber and left overnight (approx. 16 hours). Several 6.5 cm squares were cut from the hydrated VITRO-SKIN and used for absorbance measurements.

To prepare slides for testing, a minimum 100 μl of sunscreen composition is drawn or placed into a pipet tip (Justor 1100DG, set to dispense 100 μl). Using steady, even pressure on the pipette plunger, the test substance was applied to VITRO-SKIN square in a pattern of at least 50 small dots arranged to cover a 6 cm center of a square. The VITRO-SKIN square was then placed on a foam block, and the test material was spread by finger (covered with a latex glove or finger cot), first in a circular motion, then by a side-to-side motion during which the VITRO-SKIN is deformed by the pressure. The square was then mounted in a slide holder (60 mm×60 mm glassless slide mounts with metal masks by Gepe Management AG, Zug, Switzerland) and allowed to dry for 30-60 minutes.

It has been found that to avoid certain errors of an as yet unknown cause, it is advantageous to pre-expose the tested spot on the slide to 2 MED, and then zero the detector to treat the pre-exposed spot as a 0 MED reading. Thus, using the PMA 2105 UV-B detector, a pre-exposure of 2 MED was made. Immediately following the pre-exposure, the slide is taken to the UV Transmittance Analyzer and the irradiated spot is scanned. The original scan is deleted, and the new scan is saved as the baseline ("0 MED") scan.

To test stability of a slide in the UV-B range, the PMA 2105 was used, and the slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. To test stability of a slide in the UV-A range, the PMA 2114 was substituted for the PMA 2105, and a WG335 filter was installed in the beam path. The following software settings were used: UV-B=290-320 nm; UV-A=320-400 nm. Following an exposure of 5 MED, the slide was again placed in position on the UV transmittance analyzer, and a scan of the exposed spot was performed. The procedure was repeated on the same 1 cm spot on the slide until the desired total radiation dosage was achieved (approximately 35 MED for the UV-B studies, and 120 J/cm$^2$ for the UV-A studies).

FIG. 2 is a graph of the absorbance of the composition listed in Table II and the sunscreen compositions listed in Table III. As shown in FIG. 2, the sunscreen composition that does includes 2% of the Octadecene/Crylene maleate copolymer achieves the highest absorbance as compared to the sunscreen composition of Table III that does not include the polymer and the composition of Table II that includes 2% of the polymer as the only UV-absorber.

Figure 3:
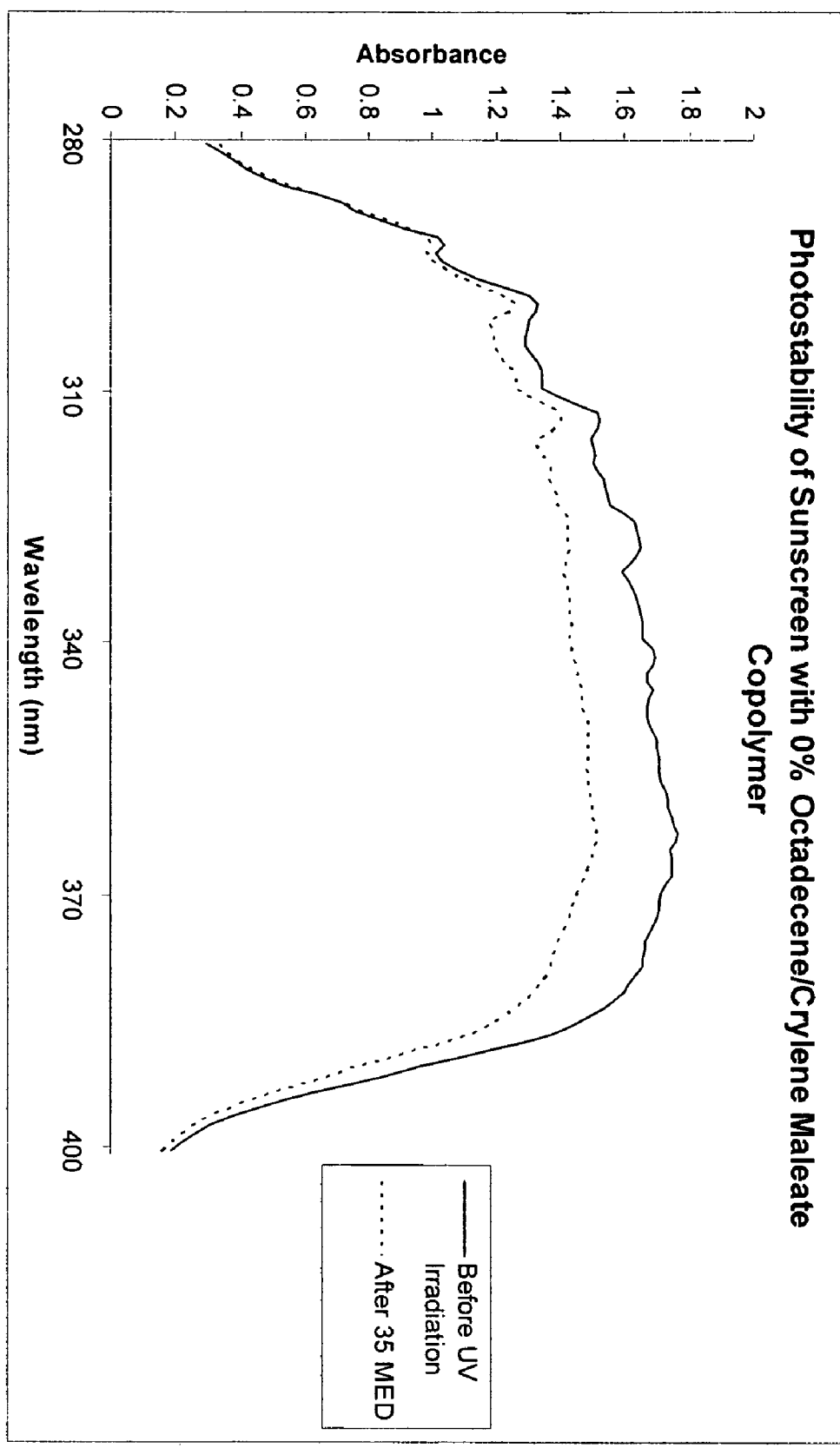
FIG. 3 is a graph of the original absorbance of a sunscreen composition that does not include Octadecene/Crylene maleate copolymer from a wavelength of 280 nm to 400 nm and after the composition has been exposed to 35 MED.

FIG. 3 is a graph of the absorbance of the sunscreen composition listed in Table III, which has no Octadecene/Crylene maleate copolymer in the composition. The absorbance spectra of the composition was recorded before and after exposure to 35 MED of radiation. As shown in FIG. 3, the sunscreen composition that does not include the Octadecene/Crylene maleate copolymer is susceptible to photodegradation at 35 MED exposure.

Figure 4:
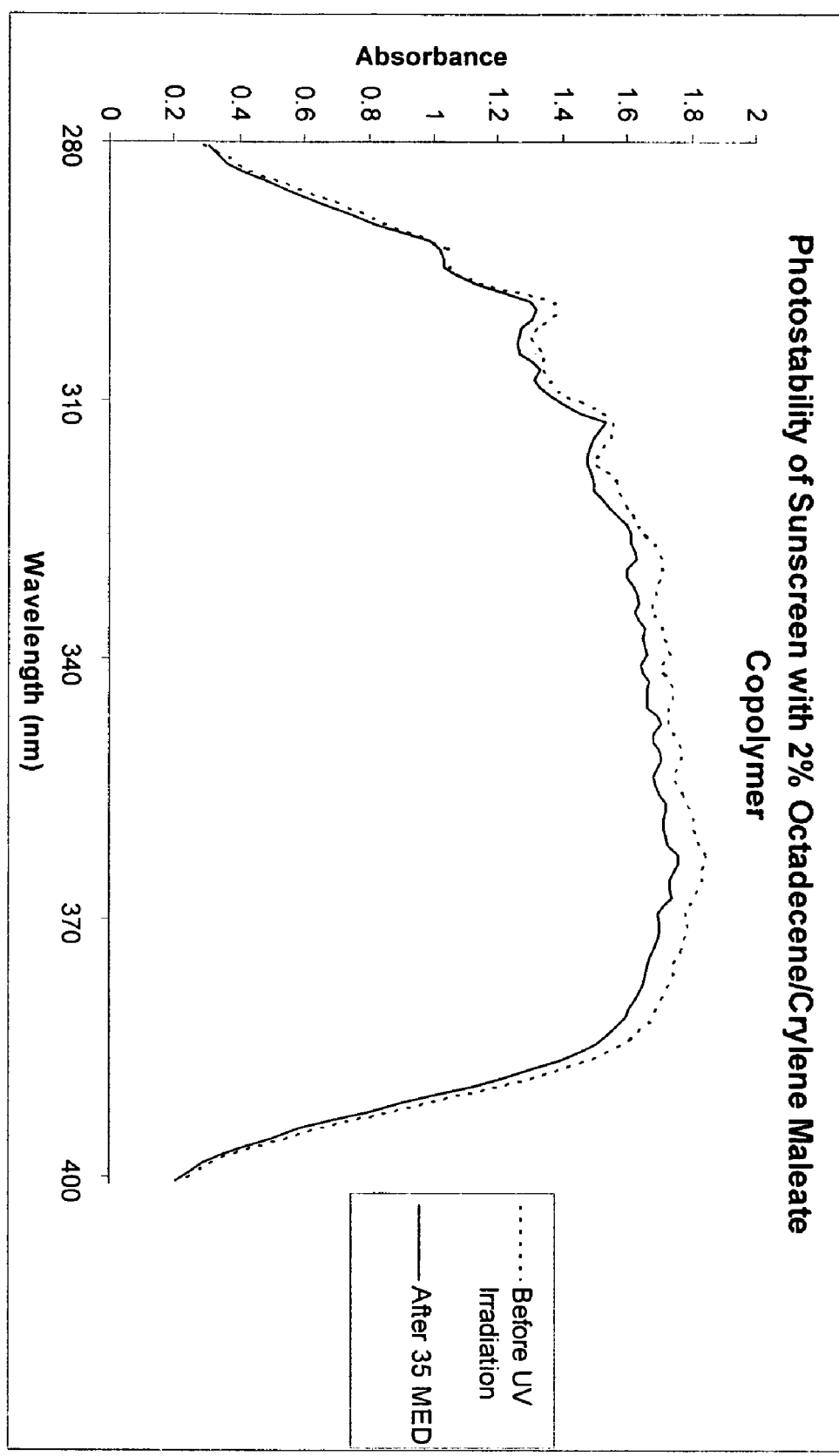
FIG. 4 is a graph of the original absorbance of a sunscreen composition that includes 2% of the Octadecene/Crylene maleate copolymer from a wavelength of 280 nm to 400 nm and after the composition has been exposed to 35 MED.

FIG. 4 is a graph of the absorbance of the sunscreen composition listed in Table III that includes 2% of the Octadecene/Crylene maleate copolymer in the composition. The absorbance spectra of the composition was recorded before and after exposure to 35 MED of radiation. As shown in FIG. 4, the absorbance spectra of the sunscreen composition of Table III that includes 2% of the Octadecene/Crylene maleate copolymer shows that the composition is relatively stable to photodegradation upon exposure to up to 35 MED.

Figure 5:
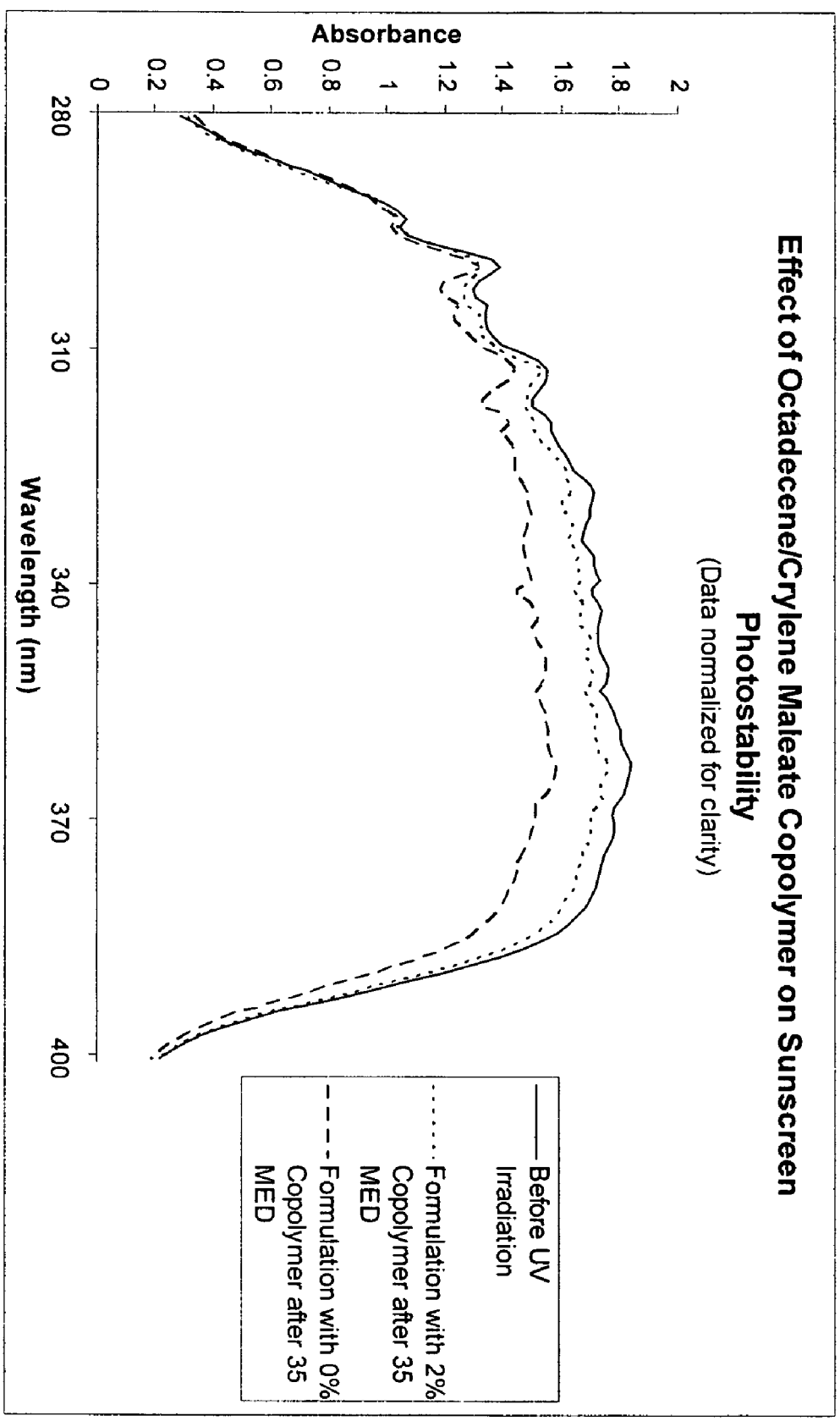
FIG. 5 is a graph of the original absorbance of a sunscreen composition including 2% Octadecene/Crylene maleate copolymer, and a sunscreen composition not including Octadecene/Crylene maleate copolymer, wherein the absorbance is measured from a wavelength of 280 nm to 400 nm and after the compositions have been exposed to 35 MED.

FIG. 5 is a graph of the absorbance of the both sunscreen compositions listed in Table III, including one that includes 2% of the Octadecene/Crylene maleate copolymer, and one that does not include the Octadecene/Crylene maleate copolymer. The absorbance spectra of compositions were recorded before and after exposure to 35 MED of radiation. As shown in FIG. 4, the Octadecene/Crylene maleate copolymer increases the photostability of the composition.

Figure 6:
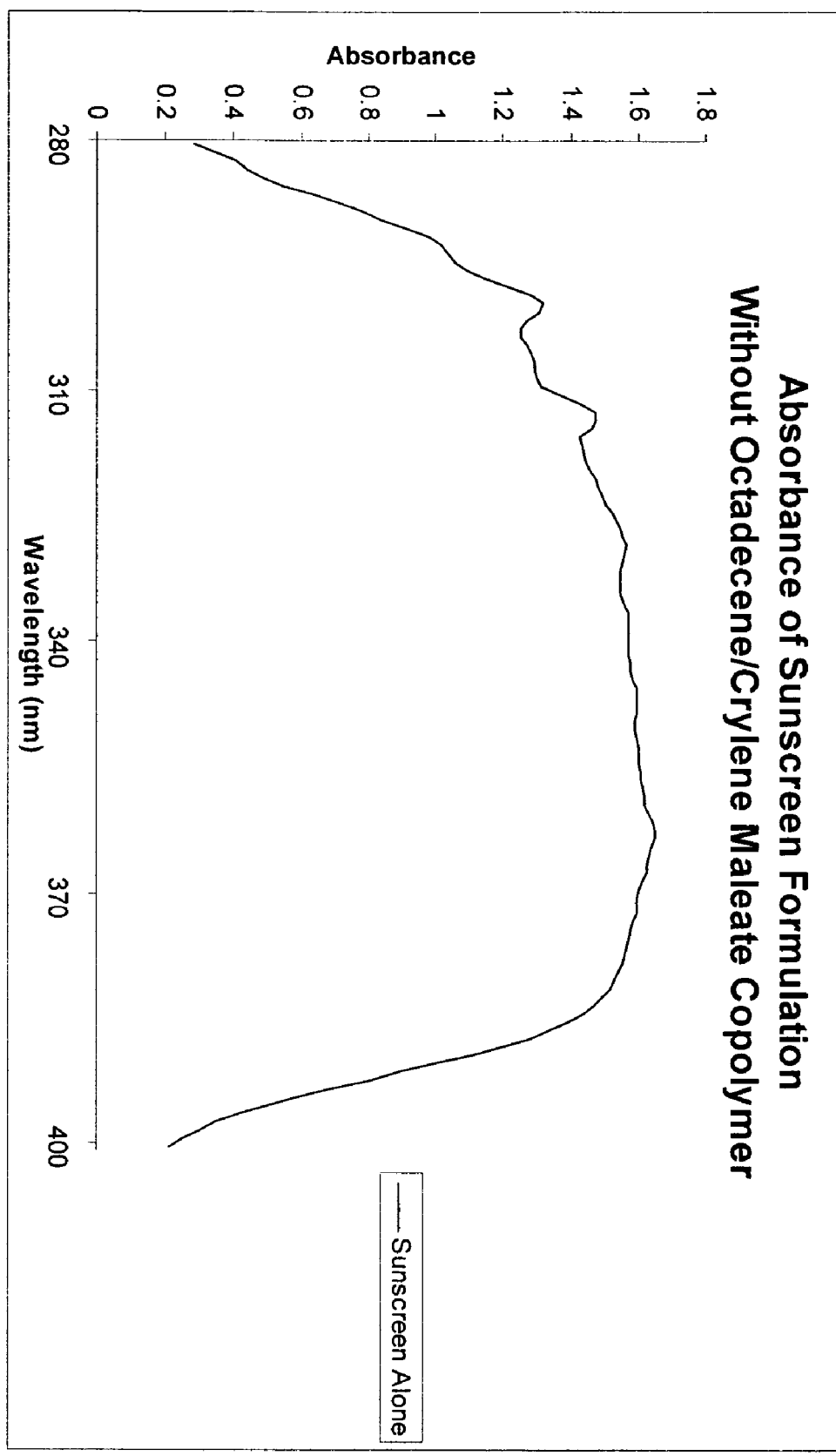
FIG. 6 is a graph of the absorbance of a sunscreen composition that does not include Octadecene/Crylene maleate copolymer, from a wavelength of 280 nm to 400 nm.
Figure 7:
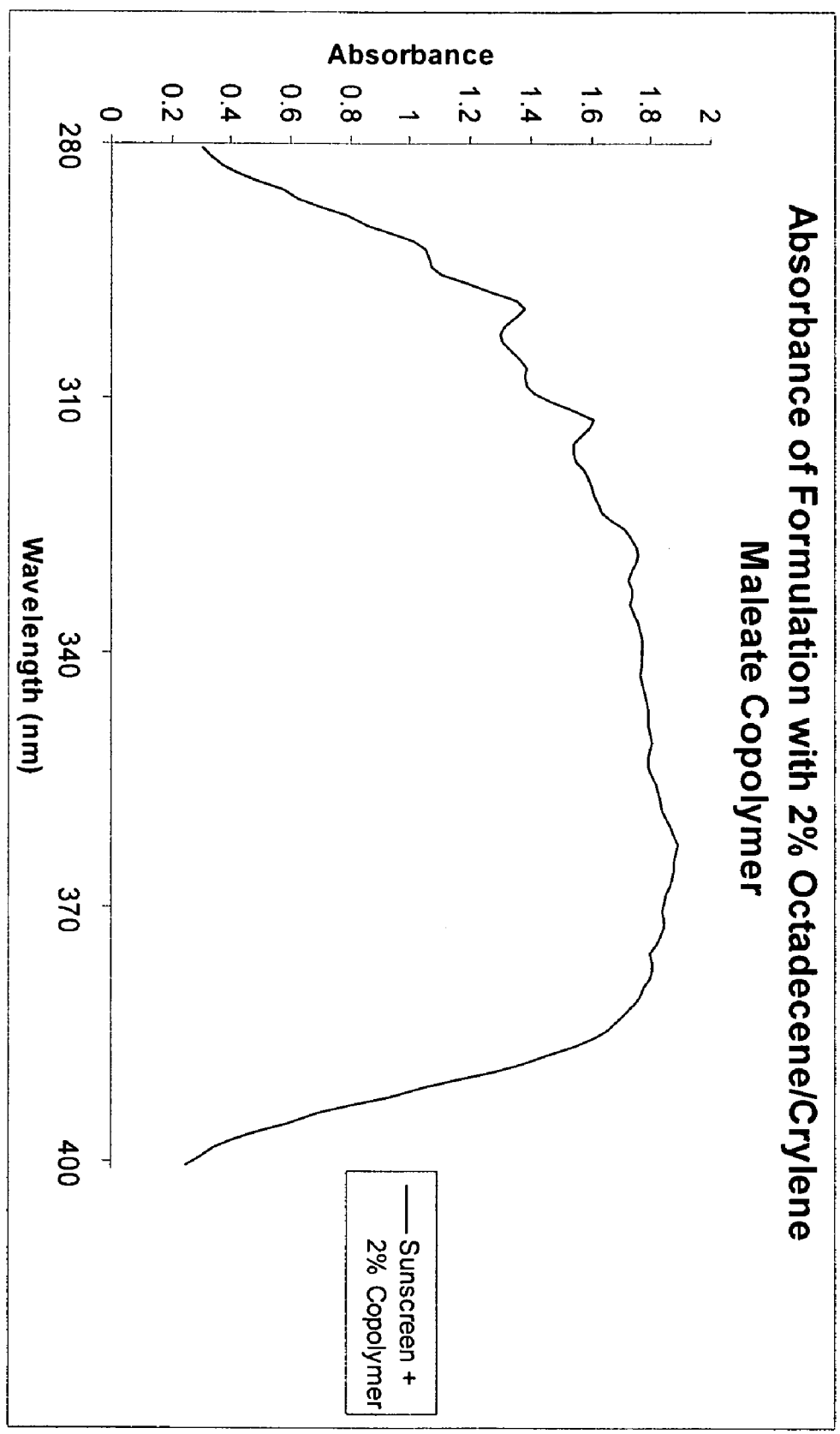
FIG. 7 is a graph of the absorbance of a sunscreen composition that includes 2% Octadecene/Crylene maleate copolymer, from a wavelength of 280 nm to 400 nm.

FIGS. 6 and 7 are the absorbance spectra for the compositions listed in Table III.

Example 4

A determination of the Sun Protection Factor (SPF) of the sunscreen compositions listed in Table II and Table III was performed. To test the SPF of the compositions, each slide was placed on the UV transmittance analyzer and scans were taken from five locations on the slide. An SPF report was generated for each slide using the Labsphere software UV1000S, Version 1.27.

The results of the SPF testing for the composition listed in Table II and the compositions listed in Table III are shown below in Table IV:

TABLE IV

| Composition | | SPF Results |
|---|---|---|
| Composition with 2% Polymer as the only UV-Absorbing Compound (Table II) | Scan No. 1 | 4.65 |
| | Scan No. 2 | 4.68 |
| | Scan No. 3 | 5.04 |
| | Scan No. 4 | 5.17 |
| | Scan No. 5 | 4.89 |
| | Average SPF | 4.9 |
| Sunscreen Composition with 0% Polymer (Table III) | Scan No. 1 | 23.32 |
| | Scan No. 2 | 21.98 |
| | Scan No. 3 | 18.96 |
| | Scan No. 4 | 23.35 |
| | Scan No. 5 | 21.88 |
| | Average SPF | 21.9 |
| Sunscreen Composition with 2% Polymer (Table III) | Scan No. 1 | 25.78 |
| | Scan No. 2 | 27.90 |
| | Scan No. 3 | 26.96 |
| | Scan No. 4 | 27.64 |
| | Scan No. 5 | 25.83 |
| | Average SPF | 26.8 |

The results shown in Table IV indicate that the addition of 2% Octadecene/Crylene maleate copolymer to a topical composition the contains no other UV absorbers provides an SPF of about 5, and provides an increase in SPF of about 5 to sunscreen compositions.

Example 5

The water resistance of sunscreen compositions listed in Table III was tested by immersing slides of VITRO-SKIN, which contain the compositions, in moving water for a period of time and testing the slides for a loss in absorbance as measured by SPF. The slides were tested before and after being immersed in water and the results were compared.

The slides were prepared according to the procedure set forth in Example 3, and each slide was placed in a beaker and the top, bottom, and sides of the slides were secured in the beaker with binder clips. The slides were then completely immersed in water by the addition of two liters of tap water to the beaker. The beaker was placed on a stir table and a stir bar is placed on the bottom of the beaker. The stir bar is set in motion to circulate the water with a mild vortex. After 40 minutes, the slides were removed from the beaker, shaken to remove excess water, and allowed to air-dry for 30 minutes. Scans are taken from five locations on the slides. The absorbance spectra and an SPF report was generated for each composition.

The results of the SPF reports are summarized in Table V below:

TABLE V

| Composition | | Pre-Immersion SPF Results | Post-Immersion SPF Results |
|---|---|---|---|
| Sunscreen Composition with 0% Polymer (Table III) | Scan No. 1 | 23.58 | 12.10 |
| | Scan No. 2 | 22.39 | 10.73 |
| | Scan No. 3 | 19.81 | 9.69 |
| | Scan No. 4 | 24.11 | 12.57 |
| | Scan No. 5 | 21.17 | 11.07 |
| | Average SPF | 22.2 | 11.2 |
| Sunscreen Composition with 2% Polymer (Table III) | Scan No. 1 | 27.09 | 29.08 |
| | Scan No. 2 | 27.77 | 29.45 |
| | Scan No. 3 | 27.23 | 29.10 |
| | Scan No. 4 | 27.29 | 29.42 |
| | Scan No. 5 | 27.74 | 28.30 |
| | Average SPF | 27.4 | 29.1 |

As shown in Table V, the immersion of the sunscreen composition containing 0% of the Octadecene/Crylene maleate copolymer in water causes a significant loss of SPF. In contrast, when the sunscreen composition listed in Table III that included 2% Octadecene/Crylene maleate copolymer was immersed in water, there was actually a slight increase in the SPF results as compared to the pre-immersion SPF results. We consider this increase to be anomalous and without significance. However, this test and the others referenced in the accompanying demonstrate the polymer's ability to: (a) provide water resistance (i.e., water proofing) to the composition, and thereby avoiding loss of the composition upon immersion; (2) absorb UV-radiation; and (3) stabilize the other photoactive compounds in the composition by, for example, absorbing the excited state energy of other photoactive compounds and rapidly dissipating that energy.

Figure 8:
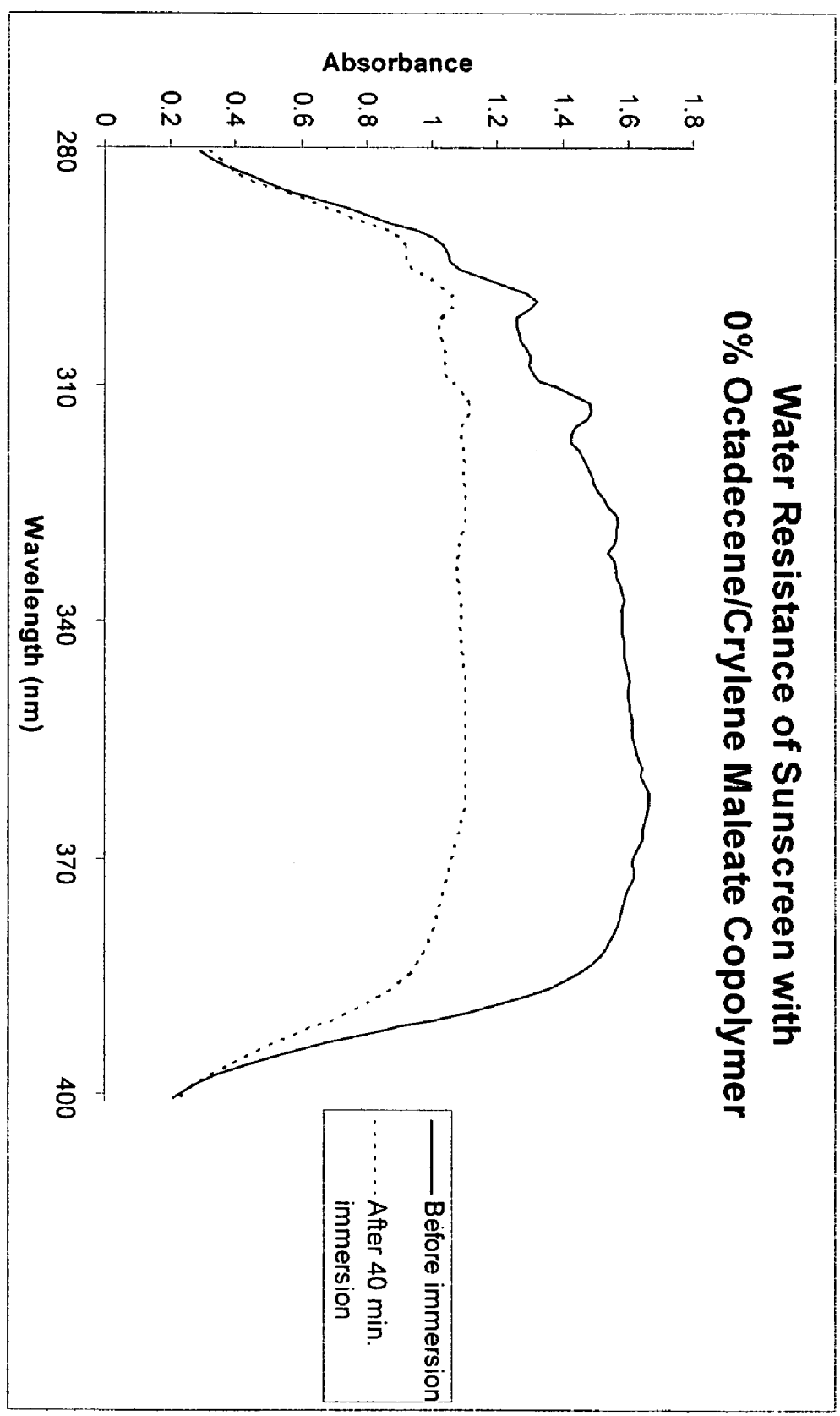
FIG. 8 is a graph of the original absorbance of a sunscreen composition that did not include the Octadecene/Crylene maleate copolymer, measuring the absorbance from a wavelength of 280 nm to 400 nm, and after the composition was immersed in water for 40 minutes.

FIG. 8 is a graph of the absorbance of the sunscreen composition listed in Table III where there is no Octadecene/Crylene maleate copolymer in the composition. As shown in FIG. 8, there is a significant loss in absorbance after the composition has been immersed in moving water for 40 minutes.

Figure 9:
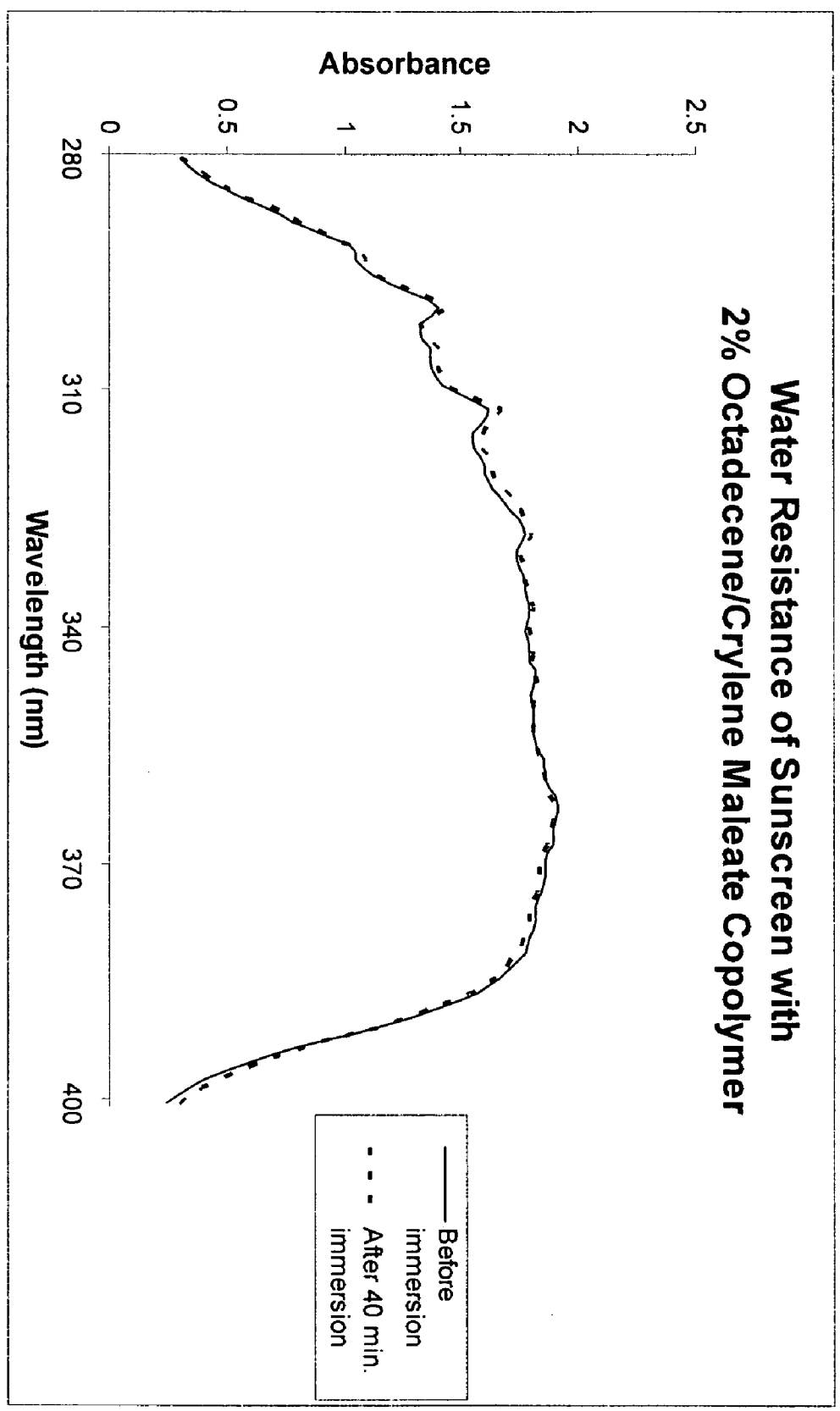
FIG. 9 is a graph of the original absorbance of a sunscreen composition that includes 2% of the Octadecene/Crylene maleate copolymer, measuring the absorbance from a wavelength of 280 nm to 400 nm, and after the composition was immersed in water for 40 minutes.

FIG. 9 is a graph of the absorbance of the sunscreen composition listed in Table III that included 2% Octadecene/Crylene maleate copolymer in the composition. As shown in FIG. 9, the absorbance spectra indicates that the immersion of the composition in moving water for 40 minutes does not cause a loss in the absorbance over the entire UV-spectra (290-400 nm).

Figure 10:
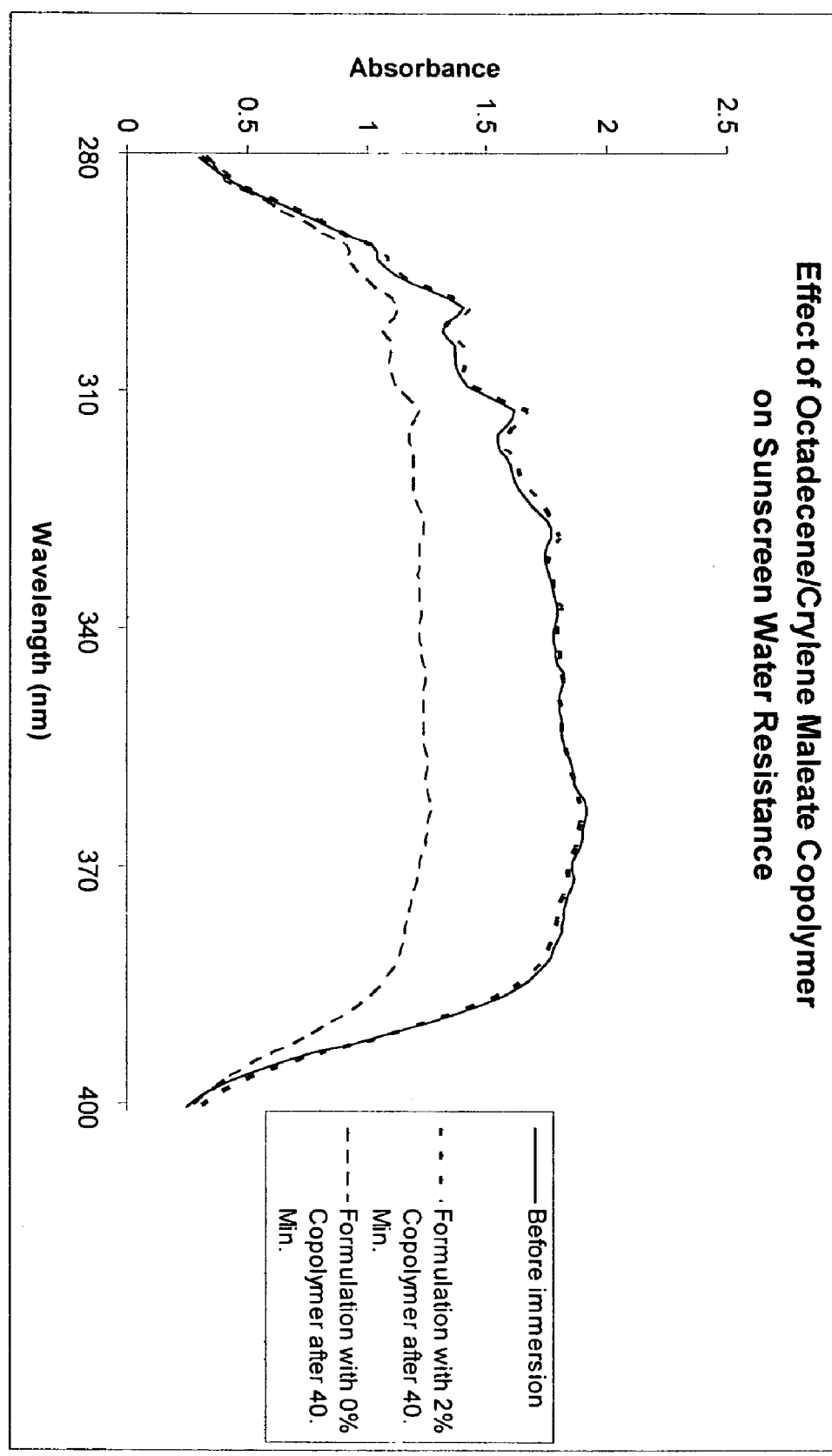
FIG. 10 is a graph of the original absorbance of a sunscreen composition that includes 2% of the Octadecene/Crylene maleate copolymer, and a sunscreen composition that did not include the Octadecene/Crylene maleate copolymer, measuring the absorbance from a wavelength of 280 nm to 400 nm, and after the compositions were immersed in water for 40 minutes.

FIG. 10 is a graph of the percent absorbance of both of the sunscreen compositions listed in Table III. As shown in FIG. 10, as compared to the composition that does not include the Octadecene/Crylene maleate copolymer, the addition of the Octadecene/Crylene maleate copolymer to the composition prevents a loss in absorbance upon immersion in moving water for 40 minutes.

The foregoing description is given for clearness of understanding only, and no unnecessary limitations should be understood therefrom, as modifications within the scope of the compounds, compositions, and methods disclosed herein may be apparent to those having ordinary skill in the art.

What is claimed is:

1. A method of protecting human skin from ultraviolet radiation comprising topically applying to said skin, in a cosmetically acceptable carrier, a composition comprising a mixture of a photoactive compound, and a compound of formula (I):

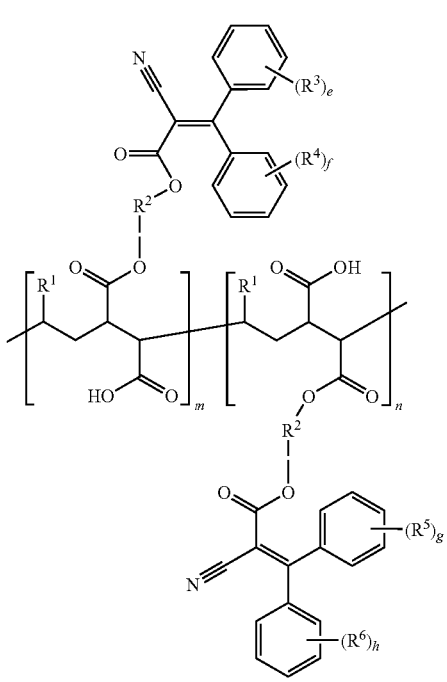

(I)

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1.

2. The method of claim 1, wherein the Weight-Average Molecular Weight of said compound of formula (1) is in the range of about 30,000 to about 110,000.

3. The method of claim 1, wherein said compound of formula (I) is present in said composition in an amount in the range of about 0.01% to about 30% by weight of the total weight of the composition.

4. A method of protecting human skin from ultraviolet radiation, comprising topically applying to said skin, in a cosmetically acceptable carrier, a compound of formula (I):

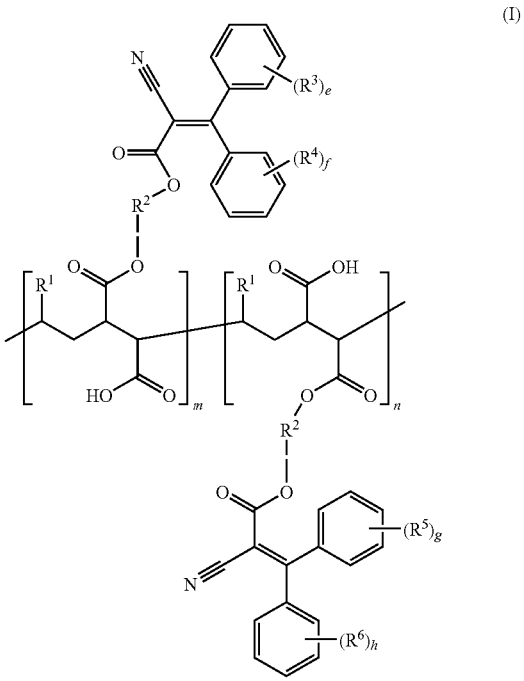

(I)

wherein $R^1$, $R^2$, $R^3$, $R^4$, $R^5$, and $R^6$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, e, g, f, and h are each in the range of 0 to 4, m and n are each in the range of 0 to 5000, and the sum of m plus n is at least 1.

5. The method of claim 4, wherein R1 and R2 are selected from the group consisting of C1-C30 alkyl groups.

6. The method of claim 5, wherein R1 is a C16 straight chain alkyl group, and R2 is a 2,2-dimethylpropyl group.

7. The method of claim 1, wherein the photoactive compound comprises a dibenzoylmethane derivative.

8. The method of claim 1, wherein the compound of formula (I) has the following formula (II):

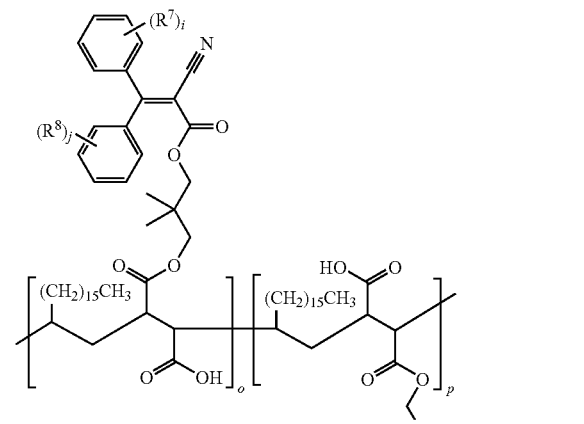

(II)

-continued

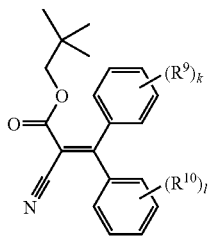

wherein $R^7$, $R^8$, $R^9$, and $R^{10}$ are the same or different and selected from the group consisting of $C_1$-$C_{30}$ alkyl, $C_1$-$C_{30}$ substituted alkyl, $C_3$-$C_8$ cycloalkyl, $C_3$-$C_8$ substituted cycloalkyl, ester, aryl, heteroaryl, heterocycloalkyl, substituted aryl, substituted heteroaryl, substituted heterocycloalkyl, cyano, and amino, i, j, k, and l are each in the range of 0 to 4, o and p are each in the range of 0 to 5000, and the sum of o plus p is at least 1.

9. The method of claim 8, wherein the Weight-Average Molecular Weight of said compound of formula (I) is in the range of about 30,000 to about 110,000.

* * * * *